(12) United States Patent  
Michaeli et al.

(10) Patent No.: US 8,152,721 B2  
(45) Date of Patent: Apr. 10, 2012

(54) RADIAL EXPANSIBLE RETRACTOR FOR MINIMALLY INVASIVE SURGERY

(75) Inventors: David Michaeli, Ashqelon (IL); Michael Michaeli, Rishon Lezion (IL)

(73) Assignee: Microdel Idea Center Ltd., Ramat Gan (IL)

( * ) Notice: Subject to any disclaimer, the term of this patent is extended or adjusted under 35 U.S.C. 154(b) by 972 days.

(21) Appl. No.: 12/097,165

(22) PCT Filed: Oct. 30, 2006

(86) PCT No.: PCT/IL2006/001250
§ 371 (c)(1),
(2), (4) Date: Jun. 12, 2008

(87) PCT Pub. No.: WO2007/069232
PCT Pub. Date: Jun. 21, 2007

(65) Prior Publication Data
US 2008/0319268 A1    Dec. 25, 2008

(51) Int. Cl.
*A61B 1/32* (2006.01)
(52) U.S. Cl. .................. 600/224; 600/202; 600/210
(58) Field of Classification Search ............. 600/210, 600/202, 224
See application file for complete search history.

(56) References Cited

U.S. PATENT DOCUMENTS

| | | | |
|---|---|---|---|
| 2,083,573 A * | 6/1937 | Morgan | 600/224 |
| 4,130,113 A * | 12/1978 | Graham | 600/224 |
| 5,081,983 A * | 1/1992 | Villalta et al. | 600/224 |
| 5,183,032 A * | 2/1993 | Villalta et al. | 600/224 |
| 5,201,325 A | 4/1993 | McEwen et al. | |
| 5,824,064 A | 10/1998 | Taheri | |
| 7,182,730 B2 * | 2/2007 | Fehling | 600/224 |
| 7,195,592 B2 * | 3/2007 | Ravikumar et al. | 600/219 |
| 7,722,570 B2 * | 5/2010 | Almond et al. | 604/167.06 |
| 7,892,173 B2 * | 2/2011 | Miles et al. | 600/210 |
| 2002/0072713 A1 * | 6/2002 | Almond et al. | 604/167.05 |
| 2003/0088157 A1 * | 5/2003 | Vassiliades et al. | 600/202 |

(Continued)

FOREIGN PATENT DOCUMENTS

FR    542744    8/1922

(Continued)

OTHER PUBLICATIONS

Extended European Search Report dated Aug. 6, 2009 issued for parallel EP Patent Application No. 06809810.2.

*Primary Examiner* — Eduardo C Robert  
*Assistant Examiner* — Stuart S Bray  
(74) *Attorney, Agent, or Firm* — The Law Office of Michael E. Kondoudis

(57) ABSTRACT

An improved radial expansible retractor and a method of minimally invasive surgery, by opening a channel in the brain or other soft tissue of a patient, by inserting the radial expansible retractor into the body of the patient, and by widening the channel at a continuous and gentle rate. The use of the improved radial expansible retractor renders surgical procedures, including neurosurgical procedures, shorter, less traumatic, and more reliable, reducing risk and the need for subsequent surgery and reducing recovery time. Procedures are carried out with real time monitoring of the retracted brain perfusion pressure. A plurality of improved radial expansible retractors may be used in a single operation. The improved radial expansible retractor allows access to areas of the brain previously almost impossible to access.

9 Claims, 11 Drawing Sheets

U.S. PATENT DOCUMENTS

| | | | |
|---|---|---|---|
| 2003/0181939 A1* | 9/2003 | Bonutti | 606/192 |
| 2004/0010208 A1 | 1/2004 | Ayad | |
| 2005/0043621 A1 | 2/2005 | Perlin | |
| 2005/0165281 A1* | 7/2005 | Ravikumar et al. | 600/204 |
| 2005/0203347 A1* | 9/2005 | Fehling | 600/210 |

FOREIGN PATENT DOCUMENTS

| | | |
|---|---|---|
| GB | 330629 | 6/1930 |
| WO | WO/01/03586 | 1/2001 |

* cited by examiner

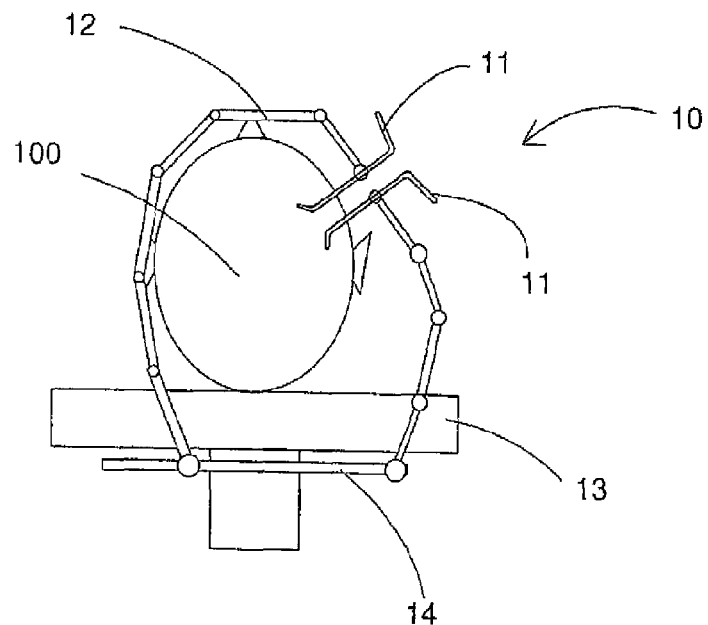
FIG. 1 PRIOR ART
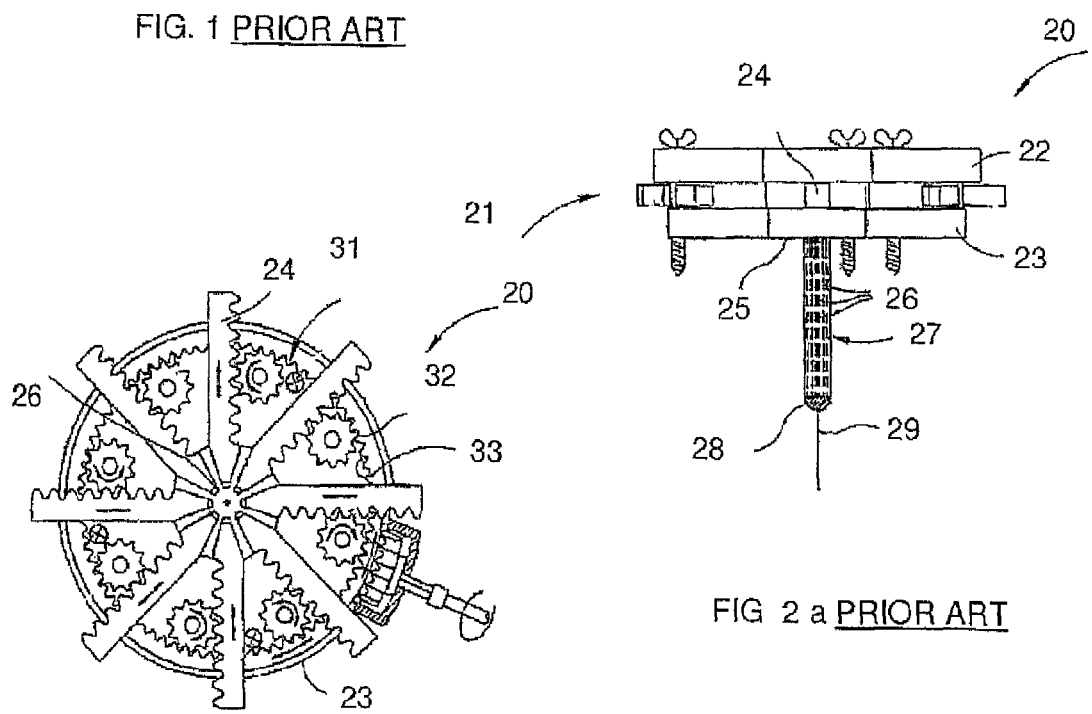
FIG 2a PRIOR ART
FIG.2b PRIOR ART

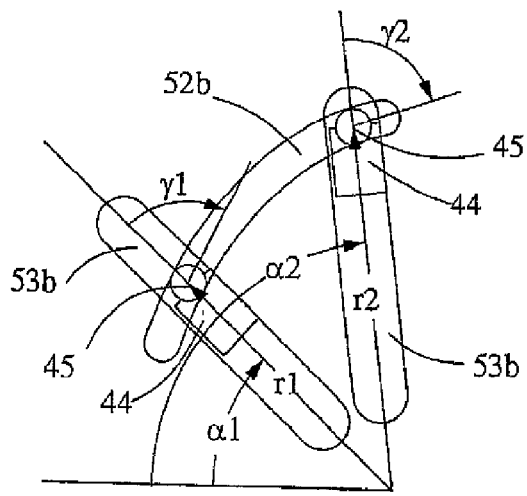
FIG. 7a
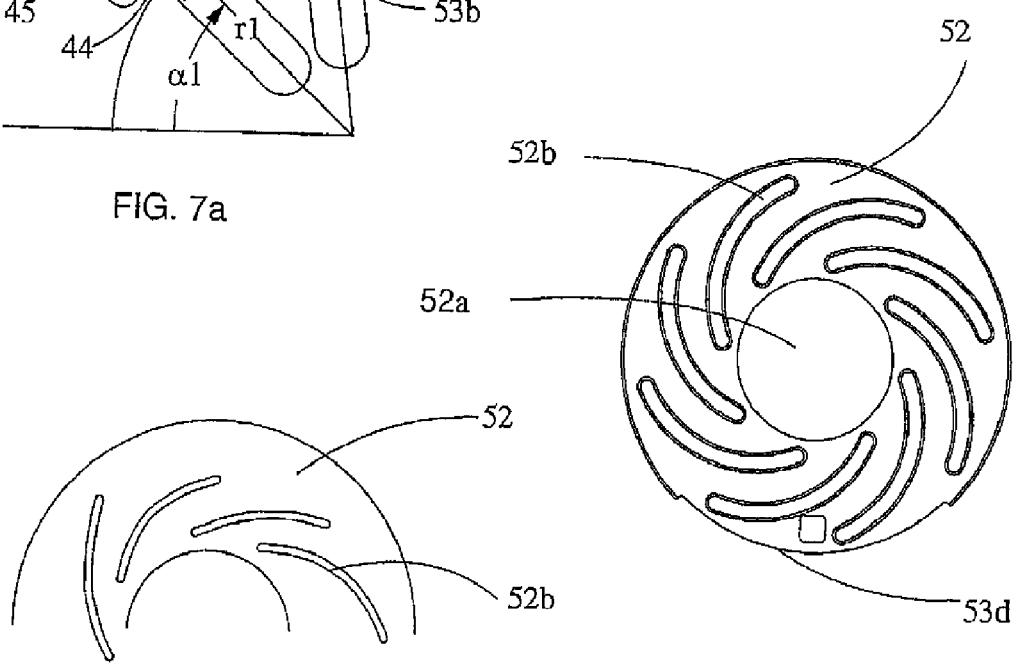
FIG. 7b
FIG. 7c
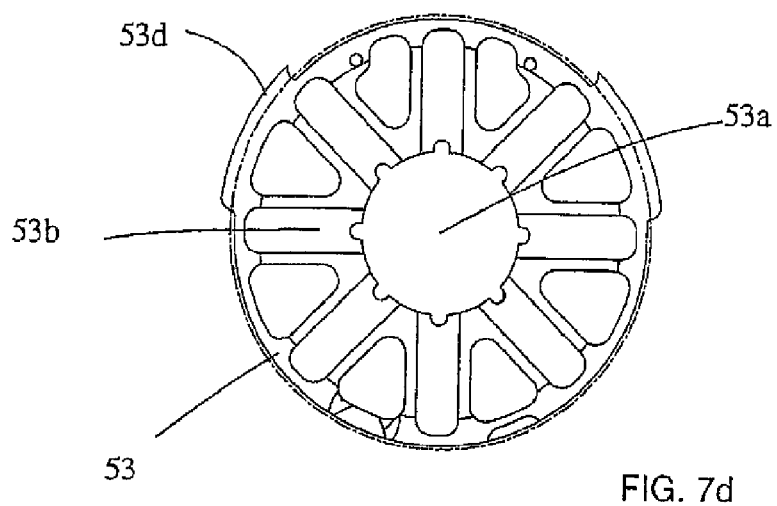
FIG. 7d

RADIAL EXPANSIBLE RETRACTOR FOR MINIMALLY INVASIVE SURGERY

FIELD AND BACKGROUND OF THE INVENTION

The present invention relates to apparatus and techniques for performing minimally invasive surgery and, in particular to a retractor device for minimally invasive surgery.

Minimally invasive surgical techniques are becoming increasingly widespread in many different surgical fields. An area in which such techniques would appear to be particularly relevant is neurosurgical removal of Space-Occupying lesions (SOL), Intra Cerebral Hemorrhages (ICH), Intra Ventricular Hemorrhages (IVH), Intra Axial Brain Tumors (IABT), Intra Ventricular Brain Tumors (IVBT), and Other Brain lesions (OBL) and Brain Pathological Conditions (BPC).

In accordance with current methods, following initial imaging for locating a brain lesion, die skull is trepanned so as to remove a bone flap exposing an opening in the skull surface, an opening of from 1 cm×1 cm tip to 5 cm×5 cm, after which retractors are inserted into the brain tissue or lobes, and used to move and draw back brain tissue or lobs in the region of the lesion, thereby exposing the brain tissue for removal.

In cases in which the region of the lesion to be removed cannot be reached, a retractor is inserted into the brain tissue and is opened slowly in order to create a channel in the brain tissue enabling access to the lesion.

After a procedure which can take many hours, the retractor is removed and the bone flap is replaced 2D or 3D Ultrasound Imaging (USI) is performed once again so as to ensure that the entire lesion has, in fact, been removed.

Existing brain retractors allow only one dimensional retraction of the brain tissue, elevating Brain Retraction Pressure (BRP) to more than 20 mg Hg causing post-operation brain edema, or severe scarring. Known current neurosurgical intervention may cause the following complications:

a. infarction of brain tissue due to the localized pressure to which the retracted portions of the brain are subjected;

b. bleeding upon insertion of the retractors;

c. if several retractors need to be inserted, the pressure on the brain tissue is uneven, the lesion may not be properly exposed, possibly leading to a need to perform supplementary surgery in order to remove any remaining tumor tissue; or d. insertion of the retractors and separation of the brain lobes are performed manually; these motions are thus inherently uneven, and are liable to cause trauma to the brain tissue.

Procedures are very lengthy and a number of surgical procedures are not carried at all out due to risk factors, or cannot be carried out successfully using current techniques. These include among others treating hemorrhage in the 4th ventricle or lateral ventricle, treating intra-ventricular hemorrhage, simultaneous removal of multiple metastases, direct treatment of brain abscess, and directly applied chemotherapy or radiotherapy of pathological tissue.

Edema caused by use of the retractor entails an increase in Intracranial Pressure (ICP), affecting the value of Cerebral Perfusion Pressure (CPP), which also depends on Mean Blood Pressure (MBP), according to the following association:

$$CPP=MBP-ICP$$

The CPP must be within the range of 50-120 mm Hg. Increased dislocation and pressure on the brainstem could cause cessation of breathing and death of the patient.

The evolution of means of opening working channels includes the following generations: The first generation used a manually opened retractor, which was also held open manually. This type of retractor also generally included two arms which open and move away from each other in linear motion. This method has several main disadvantages, including the opening applying uneven pressure on brain tissue, the retractor's force is exerted only in the single direction or single dimensional of the linear opening. Furthermore, the retractor, which is hand-held by the human operator, is insufficiently stable, and any slight tremor of the operator's hands could damage brain tissue.

The second generation used the Yasargil retractor, which is the most common means used at present.

Prof. Yasargil (now living and working in the USA) is a Turkish medical scientist and neurosurgeon. He is the inventor of the Yasargil retractor, a self-retaining brain retractor, which avoids the need for manual holding of the brain retractor.

FIG. 1 of the prior art illustrates a Yasargil retractor 10. As shown in this illustration, the head of the patient 100 is on the operation table 13, to which retractor holder 14 is attached, also including arms 12 holding a pair of spatulas 11 which are inserted in to the head when they are both close to each other and are slowly distanced from each other to enlarge the canal which was created in order to enable a view of the Space Occupation Lesion (SOL) designated for treatment, and performing the treatment itself.

In spite of the significant improvement that this means provides over the previous generation, it still does not provide sufficient uniformity of the pressure applied on the brain tissue.

The third generation is the present inventor's First Radial Expansible Retractor (FRER) for minimally invasive surgery, described in PCT/IL00/00387, filed Jul. 4, 2000, which has significant improvements which can benefit patients.

FIG. 2a of the prior art illustrates side view of a FRER 300. FRER 300 includes a FRER planar base 21, a FRER upper plate 22, a FRER lower plate 23 having a FRER central opening 25, FRER linear drive elements 24, FRER longitudinal ribs 26 comprising a FRER expansible needle shaped retractor 27, which are parallel to FRER axis 29 which is perpendicular to FRER planar base 21, and a FRER probe 28.

FIG. 2b of the prior art is a lateral cross-section view of the FRER 300 of FIG. 2a, showing the FRER expansion mechanism 31 which serves to generate the opening and closing motions of the FRER expansible needle shaped retractor, also including the FRER linear drive elements 24 and FRER outer cogwheel 32, and FRER inward facing pluralities of teeth 33 and the FRER longitudinal ribs 26.

It is of utmost importance for the retractor's opening rate to be controlled and the mechanism controlling the opening rate must be able to allow a nonlinear opening rate. Initially, the brain's resistance to the opening retractor is relatively small, and increases at a linear rate as the opening increases. A suitable opening rate at this stage is approximately 10 microns per second. Once the opening has reached a diameter of approximately 20 to 30 mm, the brain's resistance is no longer linear, and the larger the diameter, the faster the resistance increases, therefore, at this stage the opening rate must be slower, within a range of 3 to 5 microns per second, in order to prevent damage to brain tissue. Achieving such a change of rate in an opening mechanism based on cogwheels is possible only by means of changing the manual rotation rate of the external rotating wheel.

In addition, an entirely different method was demonstrated in the Cincinnati Children's Hospital Medical Center in Ohio by Dr. Crone, in which a sausage-like balloon was inserted into the brain, was gradually inflated mid kept in the brain for several days. The balloon was inflated slowly, spreading and creating a safe pathway, afterwards the inflation was ceased and the balloon was removed from the brain, leaving a gap in the brain which could be used as a working channel.

This method requires anesthetizing the patient more than once, thus increasing the risk to his life.

There is thus a widely recognized need for, and it would be highly advantageous to have, a radial expansible retractor for minimally invasive surgery which enables opening a channel while exerting force on the surrounding tissue as uniformly as possible when inserted into brain tissue, while achieving a continuous opening rate and value suitable for the respective CPP at every stage of the opening.

SUMMARY OF THE INVENTION

It is an objective of the present invention to provide the means to open a channel in the brain or any other organ of a patient, through which the area designated for treatment can be seen, and through which surgical tools can be inserted for treatment, such as extracting a tissue sample for biopsy, or performing excision or suction of tissue for the purpose of removing a cancerous tumor etc. According to the present invention, a retractor of improved performance with regard to the performance of standard retractors is used and enables performance of medical procedures in previously unattainable depths in the brain, and in a patient-friendly manner in comparison with the insertion of standard retractors into the brain, which results in less brain damage to recovering patients, as well as a lower post-operation death rate.

The retractor according to the present invention is connected stably to a device which can be attached to die operation table on which the patient is prone. After drilling a hole of a suitable diameter in the skull, in the case of brain surgery, the retractor is inserted into the patient's brain under the surveillance of an imaging system such as MRI or any other of sufficient resolution to prevent damage to brain neural fibers. After insertion into the required depth and location, the retractor is opened gently, at a suitable opening rate and force. The retractor is composed of several ribs of a suitable length creating a lateral cross section shaped compatibly with the desired cross section of the channel. Usually, when the retractor is closed, the ribs form the shape of a closed cylinder with walls of a sufficient width to ensure the necessary structural integrity, with each rib serving as a segment of the cylinder's section. For example, when the cylinder's section is circular, and the number of ribs is eight, each rib will have a cross section of a circular arc with an opening angle of 45 degrees. This structure of the retractor prevents the formation of non-uniform pressures on the different brain areas coming into contact with the retractor.

Gentle and continuous opening of the retractor is of special importance, and is achieved by gentle rotation of a disc grooved with a single groove for each rib, with a pin at the base of each rib which is inserted in the respective groove, and thus forced to move radially according to the state of the grooved disc. The forced radial motion is achieved by the disposal of the base of the rib in an adjacent channeled disc, such that rotational movement, around a joint perpendicular central rotational axis, alters the angular relation between discs, the grooved disc and the channeled disc.

Control of the rotational velocity of the grooved disc can be manual or by means of a suitable engine, assisted by a mechanical system for transmission of continuous and gentle motion.

When the retractor opens, a gap is created between the ribs, causing the creation of non-uniform pressures on the brain tissue; therefore the retractor includes a flexible sleeve external to the ribs, which stretches during opening. In the center of the retractor, between the ribs, there is a probe at whose tip in the retractor entry direction there is a half-elliptical or similarly shaped dome. This dome facilitates assembling the flexible sleeve onto the retractor ribs, and serves as the retractor's spearhead when inserting the retractor into the tissue.

Due to both the force exerted by the flexible sleeve on the ribs and the pressure of the tissue into which the retractor is inserted when opening as the ribs are distanced from each other at their base near the grooved disc, their opening near the spearhead is little or nonexistent, and the retractor assumes a shape resembling a pyramid, so that when opening is completed, therefore when opening is completed a cylinder, whose cross section has geometrical dimensions and form conforming to the retractor's cross section, is gently inserted through the base of the retractor, so that the retractor's ribs are gradually pushed away from each other until they are all parallel. This cylinder and the flexible sleeve can be composed of translucent materials which enable performing a visual survey of the tissue surrounding the retractor, by means of illumination of a suitable wavelength. Furthermore, samples can be collected from various depths of brain tissue, namely Multi Level Biopsy (MLB) of the tissue surrounding the retractor can be performed through perforations in the wall of the cylinder and the flexible sleeve.

When sufficient opening is achieved, the probe can be removed from the retractor. Note that an ultrasound probe can be used instead of a simple mechanical probe to assist in guiding the retractor during insertion.

According to the present invention, the retractor can be manufactured with ribs of a fixed length in several models and sizes, varying in rib length, rib cross section shape, and/or the initial diameter of the ribs when closed and maximal diameter to which the ribs can be opened. Furthermore, models can be manufactured in which ribs of a certain length are interchangeable with ribs of another length.

According to the present invention, the grooves dictate the opening rate for a fixed rotation speed of the external rotating wheel, and the form of the grooves' curve is determined according to the need.

Opening the retractor is safest when done with real-time monitoring of the Brain Tissue Retraction Pressure (BTRP). When the BTRP increases, the operator lowers the opening rates, and if the BTRP approaches a critical value, the operator will completely cease from opening for the necessary time interval, or even reverse and close the retractor slightly. This is done mainly to avoid damage to the Blood Brain Barrier (BBB) in order not to leave hemorrhaging as a result of torn capillary blood vessels in the brain.

At the end of the medical procedure, the retractor is gently closed and then pulled out.

Changing the direction of insertion of the improved radial expansible retractor is possible, whether in a direct path or a curved path according to the shape of the anatomical section of the operation field. Changes in the angle of insertion and in the form of curvature can be carried out during insertion simultaneously in the x, y and z planes, with 6 degrees of freedom of movement in the device at any time. The shape of the channel can be altered to accommodate curved access areas, as a tube can be made from metal that is malleable and retains a first shape until manipulated into a new shape.

The tubular opening into the depths of the brain and to other organs allows for the use of endoscopes, laparoscopes, ultrasound aspirators, laser, cryogenic techniques, and possibly even au operating microscope. Different types of coagulation and bleeding cessation devices can be inserted. Focused radiation of different types can be applied via the opening and directed onto pathological tissue with minimal damage to surrounding healthy tissue.

Neurosurgical operations have multiple applications, including but not restricted to removal of blood clots in the brain including in areas that are difficult to access such as the 4th ventricle, lateral ventricle, etc. Neuro-navigation and intra-ventricular deep brain surgery and general brain tumor therapy are possible by means of minimally invasive procedures, drastically reducing operating time and vastly improving recovery process. Double or multiple insertion of the device is possible to work independently and simultaneously in different areas of the brain. With the aid of an endoscope and light, tumors are easily removed. Negative pressure can be applied in the event of intra-ventricular hemorrhaging to alleviate pressure in the aqueduct, to prevent hydrocephalus, to suction and clean out ventricles and remove blood clots. Suction can be either contact or non-contact. Multiple metastases can be removed by a plurality of retraction devices being inserted into different areas of the brain. Ventricular peritoneal shunt that is currently inserted blindly causing damage by accidentally entering the brain ventricle can now be guided from the occipital boom to drain fluid. Procedures can be carried out under MRI.

For operation of the improved radial expansible retractor, the required size of the opening of the skull is much smaller than in prior art procedures, and the time needed to perform surgery is greatly reduced, speeding up post-operative recovery and reducing post-operative complications.

Additional objects and advantages of the invention will be set forth in part in the description which follows and, in part, will be obvious from the description, or may be learned by practice of the invention.

According to the present invention there is provided a radial expansible retractor for minimally invasive surgery for opening a channel in the brain and in any other soft tissue of a patient, by inserting part of the radial expansible retractor into the body of the patient, and by widening the channel at a continuous and gentle rate, the radial expansible retractor including: (a) a grooved disc having a central perforation, a cylindrical surface at the circumference of the grooved disc, and at least three grooves wherein the grooved disc defines an imaginary orthogonal coordinate system having X, Y, and Z axis, wherein the Z axis substantially passes through the center of the central perforation of the grooved disc, and wherein toe grooved disc substantially lays on an imaginary plane, perpendicularly to the Z axis, wherein each of the grooves have an continuous curved shape on a plane perpendicular to the Z axis, wherein each of the grooves has three dimensional geometrical shape and size; (b) a channeled disc disposed at a position relative to the grooved disc, having at least three channels, wherein the channeled disc substantially lays on an imaginary plane, perpendicularly to the Z axis, and wherein the Z axis substantially passes through the center of the central perforation of the channeled disc, wherein each of the channels has three dimensional geometrical shape and size, wherein each of the channels has a direction on a plane perpendicular to the Z axis, along a radial, wherein the radial starts at the Z axis, wherein the grooved disc can rotate at certain angle limits around the Z axis and thereby changing the position of the channeled disc relative to the grooved disc; (c) at least three ribs defining a channel having a cross sectional size, wherein each of the ribs has a base, a leading edge, and a cross section shape, wherein each of the ribs is laid substantially in parallel to the Z axis; and (d) at least three carriers wherein each of the carriers is connected to the base of one of the ribs, so that each of the ribs is connected to one of the carriers, wherein each of the carriers has three dimensional geometrical shape and size, conforming to the geometrical shape and size of the channels, wherein each of the carriers includes: (i) a pin having three dimensional geometrical shape and size, conforming to the geometrical shape and size of the grooves, wherein each of the carriers is located inside one of the channels, and wherein each of the pins is located inside one of the grooves, so that a change of a relative position of the channeled disc relative to the grooved disc, which is expressed in a change of the angle between them on the plane perpendicular to the Z axis, causes a change of distance of each of the ribs from the Z axis, while the change of distance can be performed gently and continuously.

According to further features in preferred embodiments of the present invention the radial expansible retractor further including: (e) a cover disc having a central perforation and a cylindrical wall, and wherein the Z axis substantially passes through the center of the central perforation of the cover disc, wherein the channeled disc and the cover disc together form a package inside which a grooved disc is disposed.

According to further features in preferred embodiments of the present invention the radial expansible retractor, further including: (f) at least tree bolts, wherein the each of the rib bases and each of the rib carriers has a hole and wherein each one of the bolts connect one of the rib carriers to one of the rib bases, so that each one of the rib bases is connected to one of the rib carriers and each one of the rib carriers is connected to one of the rib bases.

According to further features in preferred embodiments of the present invention the radial expansible retractor further including: (g) a tooth rail disposed on the cylindrical surface at the circumference of the grooved disc.

According to further features in preferred embodiments of the present invention the radial expansible retractor further including: (h) a handle housing disposed on the cover disc and on the channeled disc; and (i) a worm, wherein the worn is positioned inside the handle housing, adjacent to the tooth rail such that when the worm performs rotational movement around an imaginary axis on a plane perpendicular to Z axis, it transmits mechanical movement to the tooth rail, thus granting rotational movement to the grooved disc around Z axis.

According to further features in preferred embodiments of the present invention the radial expansible retractor further including: (j) a shaft disposed on the worm, inside the handle housing; (k) a front sleeve disposed around the shaft, inside the handle housing; and (l) an inner bearing disposed around the shaft, inside the handle house.

According to further features in preferred embodiments of the present invention the radial expansible retractor further including: (m) a rotating wheel disposed on the shaft.

According to further features in preferred embodiments of the present invention the radial expansible retractor further including: (m) an engine disposed on the shaft.

According to the present invention the radial expansible retractor further including: (m)

an adaptor disposed on the handle housing.

According to further features in preferred embodiments of the present invention the radial expansible retractor further including: (n) a central rod having tail and head, wherein the head has a dome shape, wherein the central rod can be inserted between the ribs and pulled out from between them; (o) a tubule, wherein the tubule can be inserted between the ribs and pulled out from between the ribs and pulled out from between them; and (p) a flexible sleeve, wherein the flexible sleeve can be pulled over the ribs and pulled off of them.

According to further features in preferred embodiments of the present invention the tubule is composed of a translucent material and has at least one perforation, and wherein the flexible sleeve is composed of a translucent material.

According to further features in preferred embodiments of the present invention each of the ribs cross section shape is circular.

According to further features in preferred embodiments of the present invention each of the ribs cross section shape is of a segment of a cylindrical wall, while the combination of all of the cross section shapes can form a cross section shape of a cylindrical wall, and wherein each of the ribs has an internal surface, and an external surface.

According to further features in preferred embodiments of the present invention the cylindrical wall shape is circular.

According to further features in preferred embodiments of the present invention the cylindrical wall shape is oval.

According to further features in preferred embodiments of the present invention the radial expansible retractor further including: (m) at least one pressure sensor disposed on the external surface.

According to further features in preferred embodiments of the present invention the radial expansible retractor further including: (m) at least one pressure sensor disposed on the external surface.

According to further features in preferred embodiments of the present invention the radial expansible retractor further including: (m) at least one pressure sensor disposed on the external surface.

According to further features in preferred embodiments of the present invention the radial expansible retractor has at least eight ribs, wherein the grooved disc has at least eight grooves, and wherein the channeled disc has at least eight channels.

According to further features in preferred embodiments of the present invention each of the grooves' continuous curves shape has the same curved shape.

According to further features in preferred embodiments of the present invention at least one of the grooves' continuous curves has a shape differing from that of at least one of the other grooves' continuous curves.

According to further features in preferred embodiments of the present invention each of the grooves' continuous curves has a first end and a second end, wherein the groove's continuous curve has a first angle measured between the continuous curve's direction at the first end and the direction of a radius starting at Z axis passing through the first end, wherein the groove's continuous curve has a second angle measured between the continuous curve's direction at the second end and the direction of a radius starting at Z axis passing through the second end, and wherein the second angle is at least three degrees larger, and at most eight degrees larger, than the first angle.

According to further features in preferred embodiments of the present invention the radial expansible retractor further including: (m) at least one subsystem for real time measurement and monitoring of the brain retraction pressure (BRP), the subsystem for measurement of the pressure on tissue including: (i) a folded bag disposed in a gap formed between two adjacent the labs; (ii) an air pipeline connected to the folded bag; (iii) an air pressure source connected to the pipeline; and (iv) an air pressure gauge connected to the pipeline, wherein the flexible sleeve has a window and wherein the folded bag is disposed facing the flexible sleeve window.

According to further features in preferred embodiments of the present invention the subsystem for measurement of the pressure on tissue, her including: (v) an electrical power source; (vi) electrical wires connected to the power source; (vii) a miniature control light bulb connected to the electrical wires; and (viii) two electrical contact elements connected to the electrical wires and attached to the insides of the folded bag such that when the folded bag is not inflated both of the contact elements touch each other and the miniature control light bulb is switched on, and when the folded bag is inflated both of the contact elements are separated from each other and the miniature control light bulb is switched off.

According to the present invention there is provided a method of minimally invasive surgery, including the steps of: (a) providing a radial expansible retractor for minimally invasive surgery for opening a channel in the brain of a patient, by inserting the radial expansible retractor into the brain of the patient, and by widening the channel at a continuously and gentle rate, the radial expansible retractor including: (i) a grooved disc having a central perforation, a cylindrical surface at the circumference of the grooved disc, and at least three grooves wherein the grooved disc defines an imaginary orthogonal coordinate system having X, Y, and Z axis, wherein the Z axis substantially passes through the center of the central perforation of the grooved disc, and wherein the grooved disc substantially lies on an imaginary plane, perpendicularly to the Z axis, wherein each of the grooves has an continuous curved shape on a plane perpendicular to the Z axis, wherein each of the grooves has three dimensional geometrical shape and size; (ii) a channeled disc disposed at a position relative to the grooved disc, having at least three channels wherein the channeled disc substantially lies on an imaginary plane, perpendicularly to the Z axis, and wherein the Z axis substantially passes trough the center of the central perforation of the channeled disc, wherein each of the channels have three dimensional geometrical shape and size, wherein each of the channels has a direction on a plane perpendicular to the Z axis, along a radial, wherein the radial starts at the Z axis, wherein the grooved disc can be rotated at certain angle limits around the Z axis thereby changing the position of the channeled disc relative to the grooved disc; (iii) at least three ribs defining a channel having a cross sectional size, wherein each of the ribs has a base, a leading edge, and a cross section shape, wherein each of the ribs is laid in parallel to the Z axis; and (iv) at least three carriers wherein each of the carriers is connected to the base of one of the ribs, so that each of the ribs is connected to one of the carrier, wherein each of the carriers has three dimensional geometrical shape and size, conforming to the geometrical shape and size of the channels, wherein each of the carriers includes: (A) a pin having three dimensional geometrical shape and size, conforming to the geometrical shape and size of the grooves, wherein each of the carriers is located inside one of the channels, and wherein each of the pins is located inside one of the grooves, so that a change of a relative position of the channeled disc relative to the grooved disc, which is expressed in a change of the angle between them on the plane perpendicular to the Z axis, causes a change of distance of each of the ribs from the Z axis, while the change of distance can be performed gently and continuously; and (v) a cover disc having a central perforation and a cylindrical wall, and wherein the Z axis substantially passes trough the center of the central perforation of the cover disc, wherein the channeled disc and the cover disc together form a package inside which a grooved disc is disposed; (b) forming an opening in an exterior of a body portion located in proximity to a tissue portion sought to be surgically removed; (c) inserting the radial expansible retractor ribs through the opening, through a body tissue so as to reach the tissue portion sought to be surgically removed; and (d) expanding the radial expansible retractor ribs by distancing them from one another in linear radial movement from a joint center to cause a lateral multi-axial displacement of adjacent tissue so as to expose the tissue portion sought to be surgically removed.

According to further features in preferred embodiments of the present invention the method of minimally invasive surgery further including the steps of: (e) removing the tissue portion sought to be surgically removed by direct contact.

According to the features in preferred embodiments of the present invention the method of minimally invasive surgery further including the steps of: (e) removing the tissue portion sought to be surgically removed by non-contact suction.

According to the present invention there is provided a method of Minimally Invasive Surgery (MIS), including die steps of: (a) providing a radial expansible retractor for minimally invasive surgery for opening a channel in the brain of a patient, by inserting the radial expansible retractor into the brain of the patient, and by widening the channel at a continuously and gentle rate, the radial expansible retractor including: (i) a grooved disc having a central perforation, a cylindrical surface at the circumference of the grooved disc, and at least three grooves wherein the grooved disc defines an imaginary orthogonal coordinate system having X, Y, and Z axis, wherein the Z axis substantially passes through the center of the central perforation of the grooved disc, and wherein the grooved disc substantially lies on an imaginary plane, perpendicularly to the Z axis, wherein each of the grooves has an continuous curved shape on a plane perpendicular to the Z axis, wherein each of the grooves has three dimensional geometrical shape and size; (ii) a channeled disc disposed at a position relative to the grooved disc, having at least three channels wherein the channeled disc substantially lies on an imaginary plane, perpendicularly to the Z axis, and wherein the Z axis substantially passes through the center of the central perforation of the channeled disc, wherein each of the channels has three dimensional geometrical shape and size, wherein each of the channels has a direction on a plane perpendicular to the Z axis, along a radial, wherein the radial start at the Z axis, wherein the grooved disc can be rotated at certain angle limits around the Z axis and thereby changing the position of the channeled disc relative to the grooved disc; (iii) at least three ribs defining a channel having a cross sectional size, wherein each of the ribs has a base, a leading edge, and a cross section shape, wherein each of the ribs is laid in parallel to the Z axis; and (iv) at least three carriers wherein each of the carriers is connected to the base of one of the ribs, so that each of the ribs is connected to one of the carrier, wherein each of the carriers has three dimensional geometrical shape and size, conforming to the geometrical shape and size of the channels, wherein each of the carriers includes: (A) a pin having three dimensional geometrical shape and size, conforming to the geometrical shape and size of the grooves, wherein each of the carriers is located inside one of the channels, and wherein each of the pins is located inside one of the grooves, so that a change of a relative position of the channeled disc relative to the grooved disc, which is expressed in a change of the angle between them on the plane perpendicular to the Z axis, causes a change of distance of each of the ribs from the Z axis, while the change of distance can be performed gently and continuously; and (v) a cover disc having a central perforation and a cylindrical wall, and wherein the Z axis substantially passes through the center of the central perforation of the cover disc, wherein the channeled disc and the cover disc together form a package inside which a grooved disc is disposed; (b) forming an opening in the exterior of a body portion located in proximity to a tissue portion in which hemorrhaging has occurred; (c) inserting an radial expansible retractor ribs through the opening, through body tissue so as to reach the hemorrhage to be suctioned out; (d) expanding the radial expansible ribs by distancing them from one another with linear radial movement from a joint center to cause a lateral multi-axial displacement of adjacent tissue so as to expose the hemorrhage; and (e) removing the hemorrhage by a suction.

According to further features in preferred embodiments of the present invention the method of minimally invasive surgery further including the steps of: (i) providing another radial expansible retractor for minimally invasive surgery for opening a channel in the brain of a patient; (j) forming another opening in an exterior of a body portion located in proximity to a tissue portion where hemorrhaging has occurred; (k) inserting another radial expansible retractor ribs through the another opening, through body tissue so as to reach the hemorrhage to be suctioned out; (l) expanding the other radial expansible retractor ribs by distancing them from one another in linear radial movement from a joint center to cause a lateral multi-axial displacement of adjacent tissue so as to expose a hemorrhage; and (j) removing the hemorrhage.

According to further features in preferred embodiments of the present invention the method of minimally invasive surgery further including the steps of: (e) monitoring pressure exerted on the radial expansible retractor, at least at one point of contact with a tissue during a surgical procedure, allowing a surgeon to minimize the gaps between the radial expansible retractor ribs to lower pressure, if necessary.

According to further features in preferred embodiments of the present invention the method of minimally invasive surgery further including the steps of: (f) monitoring pressure exerted on the radial expansible retractor, at least at one point of contact with a tissue during a surgical procedure, allowing a surgeon to minimize the gaps between the radial expansible retractor ribs to lower pressure, if necessary.

According to further features in preferred embodiments of the present invention the folded bag is a folded polyethylene bag.

According to further features in preferred embodiments of the present invention the electrical power source of the subsystem for measurement of the pressure on tissue, is a battery.

BRIEF DESCRIPTION OF THE DRAWINGS

The invention is herein described, by way of example, only, with reference to the accompanying drawings, wherein:

FIG. 1 of the prior art illustrates a Yasargil retractor.

FIGS. 2a and 2b of the prior art are schematic illustrations of the present inventor's first radial expansible retractor.

FIGS. 5b, and 5c are lateral section schematic illustrations of the improved radial expansible retractor of FIG. 5a.

FIG. 7a is a geometrical description of the principle of granting radial movement to a rib.

FIG. 7b is a geometrical description of the principle of granting radial movement to ribs creating an oval aperture form, of a preferred embodiment of an improved radial expansible retractor according to the present invention.

FIGS. 7c and 7d are schematic top view illustrations of a grooved disc and a channeled disc, respectively, of a preferred embodiment of an improved radial expansible retractor according to the present invention.

DESCRIPTION OF THE PREFERRED EMBODIMENTS

Figure 3A:
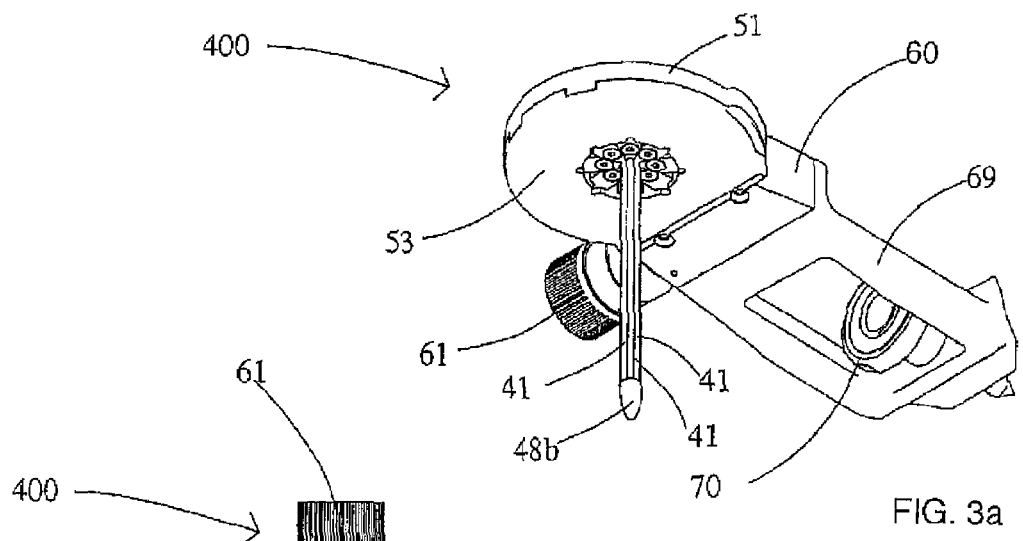
FIGS. 3a, 3b, and 3c are schematic illustrations of a preferred embodiment of an improved radial expansible retractor in a close mode according to the present invention.

The present invention is an Improved Radial Expansible Retractor (IRER) for Minimally Invasive Surgery (MIS).

The principles and operation of an IRER according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings.

Unless otherwise defined, all technical and scientific terms used herein have the same meaning as commonly understood by one of ordinary skill in the art to which this invention belongs. The materials, dimensions, methods, and examples provided herein are illustrative only and are not intended to be linking.

The following list is a legend of the numbering of the application illustrations:

11 spatula
12 arm
13 operation table
14 Yasargil retractor holder
21 FRER planar base
22 FRER upper plate
23 FRER lower plate
24 FRER linear drive elements
25 FRER central opening
26 FRER longitudinal rib
27 FRER expansible needle shaped retractor
28 FRER probe (can also include ultrasound probe)
29 FRER axis
32 FRER outer cogwheel
33 FRER outward facing pluralities of teeth
40 pressure sensor
41 rib
41a rib leading edge
41b rib external surface
41c rib internal surface
42 rib base
43 rib base hole
44 rib carrier
45 rib carrier pin
46 rib carrier hole
47 rib carrier bolt
48 central rod
48a central rod tail
48b central rod head dome
49 tubule
49a tubule perforation
50 flexible sleeve
50a flexible sleeve window
51 cover disc
51a cover central perforation
51b cylindrical wall of cover disc
51c protuberances
51d cover disc bolt holes
52 grooved disc
52a grooved disc central perforation
52b groove
52c external surface
52d depression
53 channeled disc
53a channeled disc central perforation
53b channel
53c channeled disc bolt holes
53d protrusion
60 handle housing
61 rotating wheel
62 measure wheel
63 shaft
64 front sleeve
65 worm
66 inner bearing
67 tooth rail
68 adaptor bolt
69 adaptor
70 fixation bolt 71 engine
81 holder device
82 lock
83 skull clamp
84 endoscope
85 doctor eye
86 suction device
90 folded bag
91 air pressure source
92 pipeline
93 air pressure gauge
94 electrical power source
95 miniature control light bulb
96 electrical wire
97 electrical contact element
98 subsystem for measurement of the pressure on tissue
99 aspirator
100 patient head
101 lateral ventricle
102 fourth ventricle
103 hemorrhage
104 Intra Cerebral Hemorrhage (a) (ICH)
105 Intra Ventricular Hemorrhage (IVH)
106 Intra Cerebral Hemorrhage (b) (ICH)
107 Intra Ventricular Lesions (IVL)
200 Yasargil retractor
300 First Radial Expansible Retractor (FRER)
400 Improved Radial Expansible Retractor (IRER)

Figure 3B:
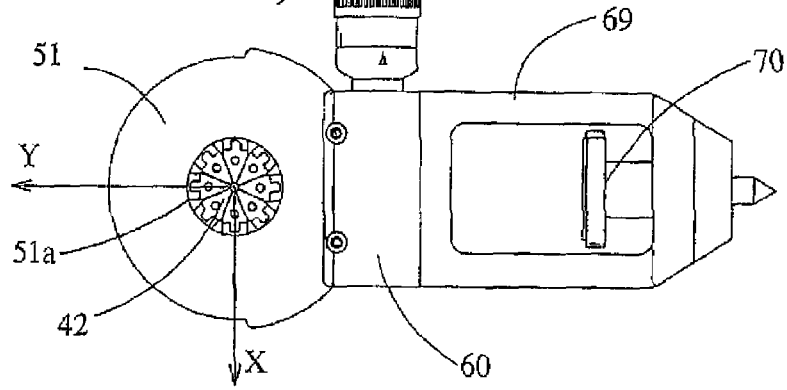
Figure 3C:
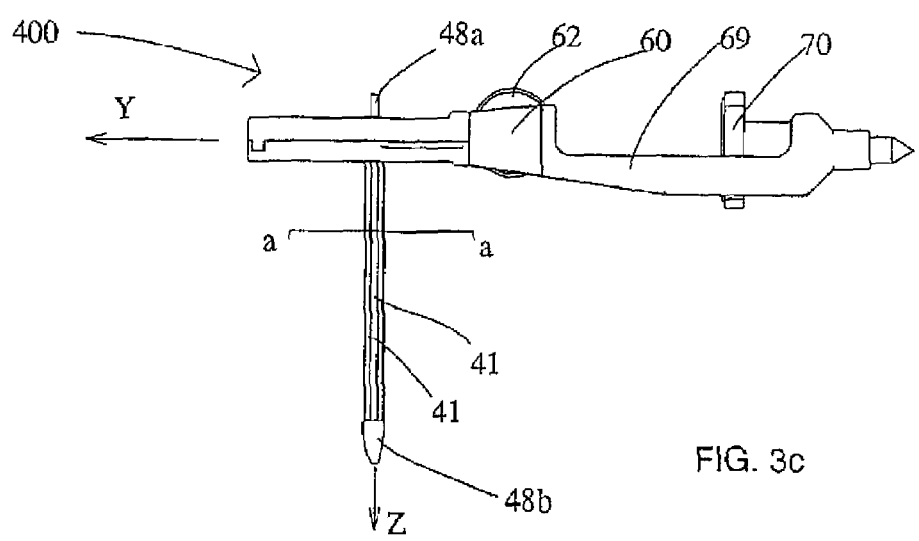

Referring now to the drawings, FIGS. 3a, 3b, and 3c are schematic illustrations of a preferred embodiment of an improved radial expansible retractor 400 in a closed mode according to a preferred embodiment of the present invention.

FIG. 3a is a perspective view, FIG. 3b is a top view, and FIG. 3c is a side view.

The illustrations show ribs 41 touching each other, and in the illustrated case, forming a hollow cylinder with walls of a thickness which, combined with the material composing ribs 41, grants the necessary strength for channel dilatation within tissue.

The quantity of ribs 41 can vary, in the preferred embodiment shown in this illustration and in those following; there are eight. The shape of the lateral section of the formed cylinder can also vary, in the preferred embodiment shown in this illustration and those following; it is circular, unless specifically noted otherwise.

In the center between the ribs 41 there is a central rod 48 whose end facing the retractor's direction of insertion has a half-elliptical or similarly shaped dome 48b. This dome facilitates pulling the flexible sleeve onto the retractor ribs and serves during insertion of the retractor into tissue, as the spearhead leading the retractor. The tail of the central rod 48a protrudes above the cover 51 and enables removal of the central rod 48a when the aperture of the ribs 41 is sufficiently wide.

Improved radial expansible retractor 400 is equipped with an adaptor 69 which, by means of fixation bolt 70, can connect the retractor to the arm of a holder device. The adaptor 69 and the handle house 60 form the retractor base, which contains a mechanism transmitting gentle rotational mechanical movement from rotating wheel 61 to a grooved disc not shown in these illustrations, within a casing whose bottom is a channeled disc 53 and is closed at the top with cover 51.

Rotating wheel 61, according to the embodiment shown in the illustration is rotated by the operator's right hand. An improved radial expansible retractor 400 can be manufactured such that the rotating wheel 61 is disposed to enable rotation by the operator's left hand.

A measuring wheel 62 marked with measurement lines can be disposed next to rotating wheel 61.

According to another preferred embodiment of the present invention, in lieu of manual operation, the rotational movement is generated by an engine.

FIG. 5b shows central perforation 51a in cover 51. The center of central perforation 51a can be the origin of an imaginary orthogonal coordinate system, fixed to the improved radial expansible retractor 400, with imaginary longitudinal axis Z, and with imaginary X and Y axes defining an imaginary plane, perpendicular to the imaginary longitudinal axis Z. The origin of such an imaginary orthogonal coordinate system can also be in other locations, such as the center of grooved disc central perforation 52a, or the center of channeled disc central perforation 53a, (52a and 53a are not seen in the present figure). Rib bases 42, in this case eight, can be seen through central perforation 51a.

FIG. 3c is marked with section line a-a.

Figure 4A:
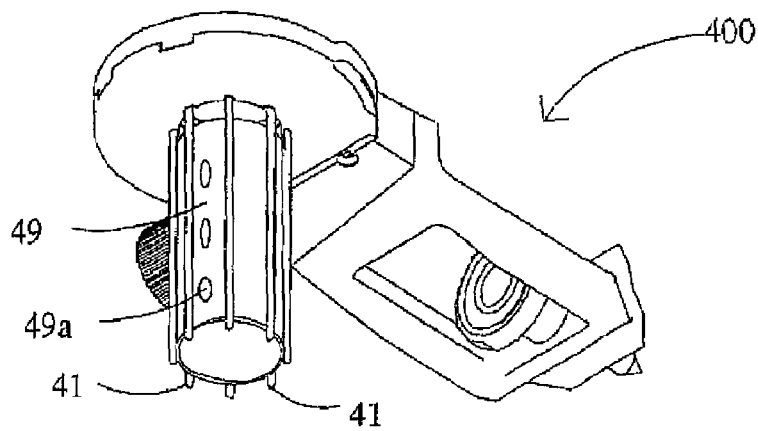
FIG. 4a is a schematic perspective view illustration of a preferred embodiment of an improved radial expansible retractor in an open mode according to the present invention.

FIG. 4a is a schematic perspective view illustration of a preferred embodiment of an improved radial expansible retractor 400 in an open mode according to the present invention.

The illustration shows a state in which the eight ribs 41 are distanced from each other, and tubule 49 passes between them. Tubule 49 can be translucent and its walls can have perforations 49a in its walls, for the purpose of illuminating the surrounding tissue with light in the visible range or any other wavelength range, by means of a light source for viewing the state of the tissue, and for performing Multi Level Biopsy (MLB).

Insertion of the tubule 49 between the ribs 41 is done after fall opening is completed gently and at a sufficiently gentle rate to ensure prevention of any undesired increase in pressure on the surrounding tissue. The lateral section of tubule 49 conforms to the lateral section of the aperture formed by the open ribs 41 and the geometrical dimensions of tubule 49 conform to the specific aperture of the ribs 41, such that when the tubule 49 is inserted, the ribs 41 are gradually distanced from each other for their entire lengths until they are parallel to each other.

Prior to removal of die improved radial expansible retractor 400, tubule 49 is removed and a closing process is performed in which the ribs 41 are drawn closer to each other, preferably to the point of touching each other and once again forming a closed shape.

Figure 4B:
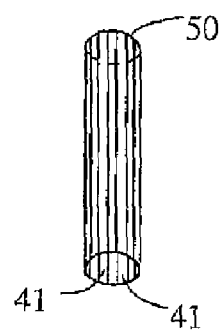
FIG. 4b is a schematic perspective view illustration of a flexible sleeve of a preferred embodiment of an improved radial expansible retractor according to the present invention.

FIG. 4b is a schematic perspective view illustration of a flexible sleeve 50 of a preferred embodiment of an improved radial expansible retractor according to the present invention.

The flexible sleeve 50 is pulled over the ribs 41 and expands as the ribs grow further apart. The lateral section of the flexible sleeve 50, in working mode, is determined by combining its elastic qualities, the pressure exerted upon it by the surrounding tissue, the shape of the ribs 41, and the shape of the tubule 49, after it is inserted between the ribs 41.

Tubule 49 and the flexible sleeve 50 are disposable, minimizing infections. The ribs 41 may be disposable, too.

Figure 5A:
FIG. 5a is a schematic top view illustration of a preferred embodiment of an improved radial expansible retractor according to the present invention.
Figure 5:
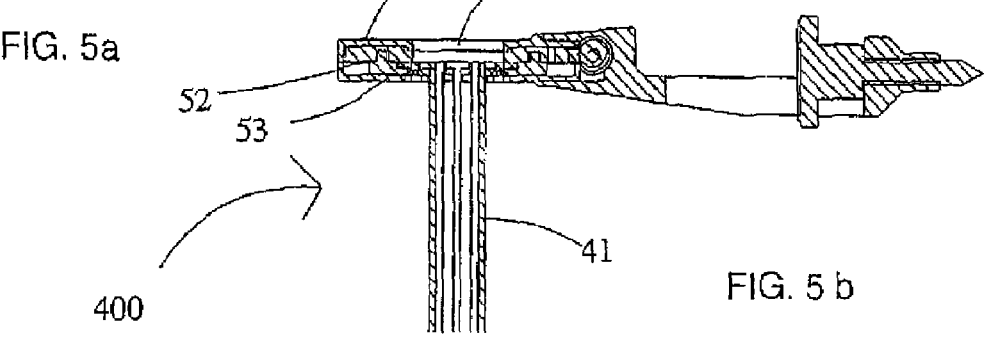

FIG. 5a is a small-scale schematic top view illustration of a preferred embodiment of an improved radial expansible retractor 400 according to the present invention, marked with cross section line b-b.

FIG. 5b, is a schematic cross section illustration of the improved radial expansible retractor 400 of FIG. 5a along line b-b.

The illustration also shows cover 51, including cover central perforation 51b, grooved disc 52, channeled disc 53, and ribs 41.

Figure 5C:
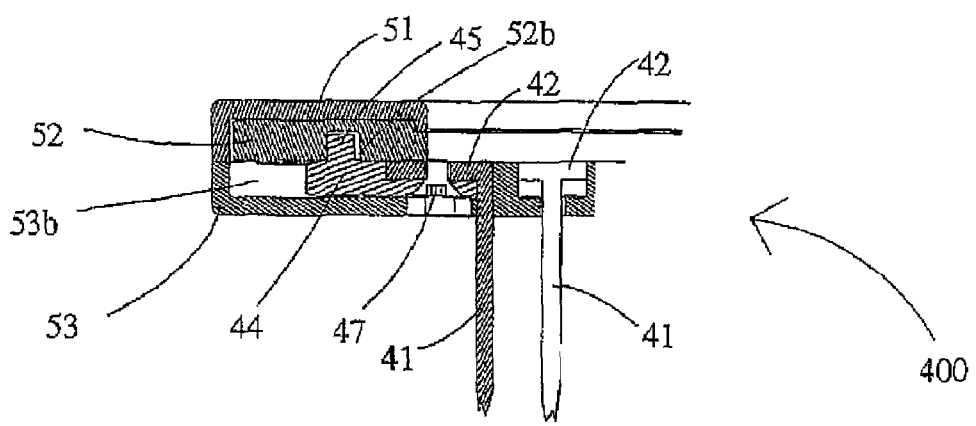

FIG. 5c shows an enlarged segment of FIG. 5b clearly showing rib carrier 44 disposed within channel 53b of the channeled disc 53, with the rib carrier pin 45 disposed within groove 52b of the grooved disc 52 whose center has a perforation 52a (not shown in the present figure) of a suitable diameter for inserting the tubule and performing the medical procedure. A series of similar perforations 51a, 52a, and 53a (not shown in the present figure) can be found in the centers of the cover 51, the grooved disc 52, and the channeled disc 53 respectively, with the centers of these three perforations disposed on a single axis. The rib carrier 44 connects to rib base 42 which is the integral base of arm 41, by means of rib carrier bolt 47.

Figures 6A, 6B, 6C:
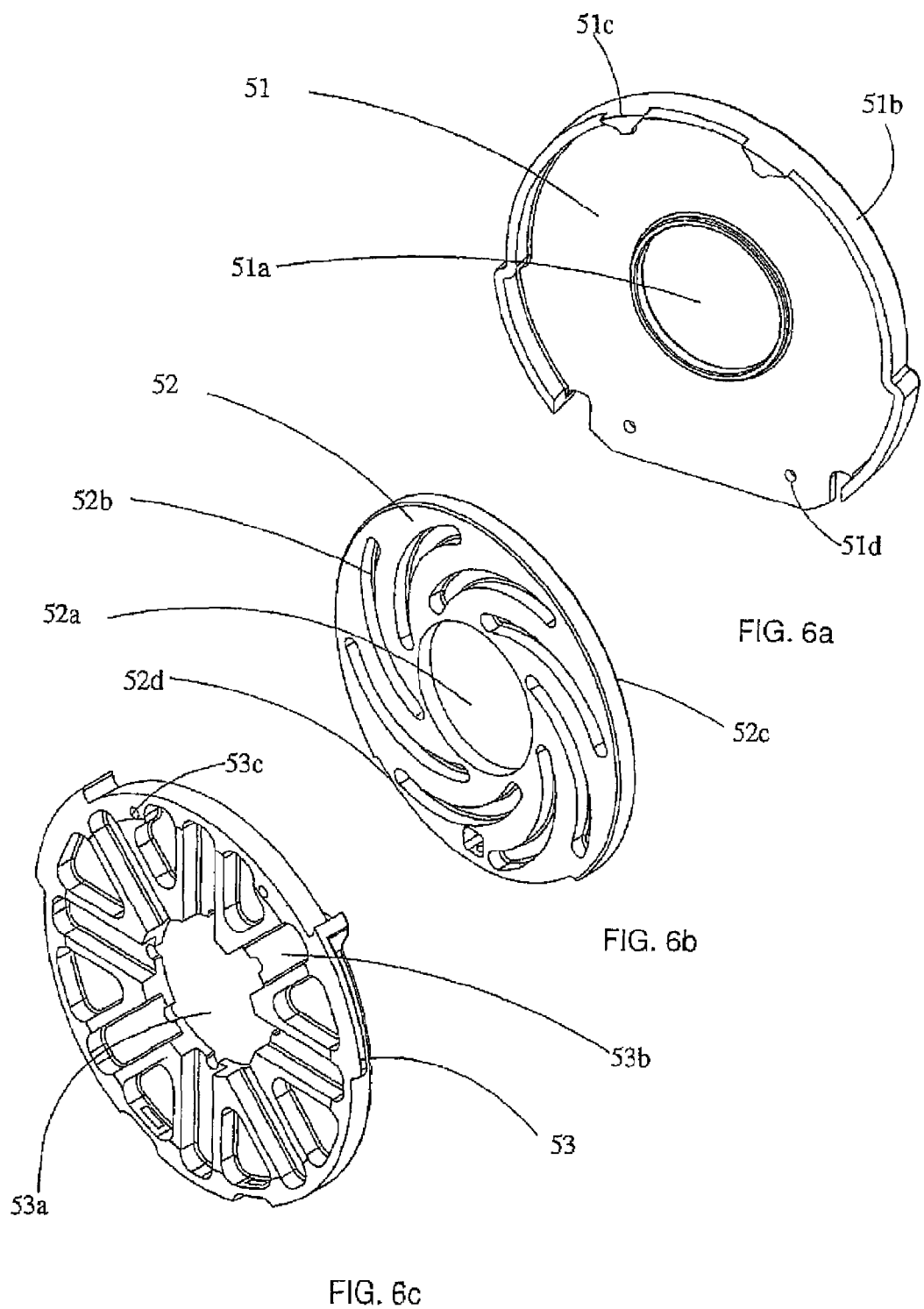
FIGS. 6a, 6b, and 6c are schematic perspective view illustrations of a cover, a grooved disc, and a channeled disc, respectively, of a preferred embodiment of an improved radial expansible retractor according to the present invention.

FIG. 6a is a schematic perspective view illustration of cover 51 in whose center is perforation 51a of a suitable diameter for inserting the tubule and performing the medical procedure, of a preferred embodiment of an improved radial expansible retractor according to the present invention.

Cover disc 51 can have a cylindrical wall 51b over part of its circumference, and this wall can have protuberances 51c for connection to channeled disc 53 shown in detail in FIG. 6c, furthermore there can be holes 51d in cover disc 51 designated for fitting connective bolts into them.

FIG. 6b is a schematic perspective view illustration of grooved disc 52, of a preferred embodiment of an improved radial expansible retractor according to the present invention, in whose center is perforation 52a, of a suitable diameter for inserting the tubule and performing the medical procedure, and grooves 52b, in the present case eight, designated to grant continuous forced movement to the rib carrier pin.

Grooves 52b can run the entire depth of the grooved disc, or a partial depth and at a suitable width, all conforming to the dimensions of the rib carrier pin.

Along the circumference of the grooved disc 52, there is an external surface 52c, a part of which can be shaped as a depression 52d designated and suitable for connection of a tooth rail to it.

FIG. 6c a is a schematic perspective view illustration of channeled disc 53 of a preferred embodiment of an improved radial expansible retractor according to the present invention, in whose center is perforation 53a, of a suitable diameter for inserting the tubule and performing the medical procedure, and channels 53b, in the present case eight, designated to grant continuous forced movement to the rib carrier 44 (not shown in the present figure). The channels 53b are completely straight, and are pointed in the directions of the radiuses from a joint center of the channeled disc 53. Their dimensions conform to those of rib carrier 44, and they are designated to enable strictly radial movement of rib carrier 44 with regard to the aforementioned center.

The channeled disc 53 can be designed and manufactured in a structure of optimal volume and weight.

Combination of the channeled disc 53 and the cover 51 is done by means of geometrically conforming both to each other, together forming a casing suitable for carrying grooved disc 52 and granting it smooth rotational movement. Closure of the casing can use suitable protuberances and depressions and part of the structures of the channeled disc 53 and the cover 51 as well as small bolts. Channeled disc 53 has bolt holes 53c.

FIG. 7a is a geometrical illustration showing the principle of granting the rib with radial motion. The illustration shows two angular relations between the groove 52b and the channel 53b. In the first state, the channel 53b is at an angle of α1 to an arbitrary reference line, and in the second state, the channel 53b is at an angle of α2 to the same reference line. The angles are measured from a joint center.

Seeing as the rib carrier pin 45 at the base of the rib is forced to be in the groove, and the base of the rib is forced to be in the channel, in the first state the rib carrier pill 45 is at a radius of r1 from the center, and in the second state the rib carrier pin 45 is at a radius of r2 from the same center. Namely, the connected rib carrier pin 45 and the rib carrier 44, as well as the rib connected to them are, in each state, at a different distance from the center, which is the center of rotation between the grooved disc and the channeled disc, and seeing as the channel 53b is radial, the rib's motion will also be radial.

As explained in the summary, it is of utmost importance for the retractor's opening rate to be controlled, and the mechanism controlling the opening rate must be able to allow a nonlinear opening rate.

The velocity of the radial movement of rib carrier pin 45 for a fixed rotational speed of groove 52b depends upon several factors, including the distance from the center of rib carrier pin 45 at the given time. The larger this distance, the larger the radial velocity, and the more perpendicular the tendency angle of groove 52b, namely the closer to the radius direction, the larger the radial velocity, while the more horizontal the tendency angle of groove 52b, namely the closer to the direction tangent to the rotational movement, the smaller the radial velocity.

In the case shown in the illustration, the tendency angle between radius r1 and groove 52b at their intersection point is γ1 while the tendency angle between radius r2 and groove 52b at their intersection point is γ2 while γ1<γ2.

FIG. 7b is a geometrical description of the principle of granting radial movement to the ribs forming a not-circular aperture form. The illustration shows four grooves 52b out of eight, which are responsible for the movement of four ribs. As shown, each of the grooves has a different curve, and each groove ends at a different distance from the center. This difference necessarily results in different movement of each of the ribs, forming a lateral section which is not circular.

FIG. 7c, is a schematic top view illustration of a grooved disc 52 of a preferred embodiment of an improved radial expansible retractor according to the present invention. The illustration shows the central perforation 52a, eight grooves 52b, and a depression 53d designated to enable good connection of the disc to the tooth rail.

In this case, the curves of all of the grooves 52b are identical and therefore the aperture of the ribs will be circular. Design and selection of the groove curve can be done by means of either trial and error or analytical calculations. The factors affecting the desired curve also include: geometrical location possibilities, depending on the dimensions of the grooved disc 52 and the width of the groove 52b, the desired radial velocity for each distance of the rib from the center, and tendency angle limitations of the groove 52b curve to allow moving rib carrier 44 to require no more than reasonable force.

FIG. 7d is a schematic top view illustration of a channeled disc 53 of a preferred embodiment of an improved radial expansible retractor according to the present invention. The illustration shows the central perforation 53a, eight radial channels 53b, and two protrusions 53d suitable for the movement of tooth rail 67 along with the grooved disc 52.

Figure 8:
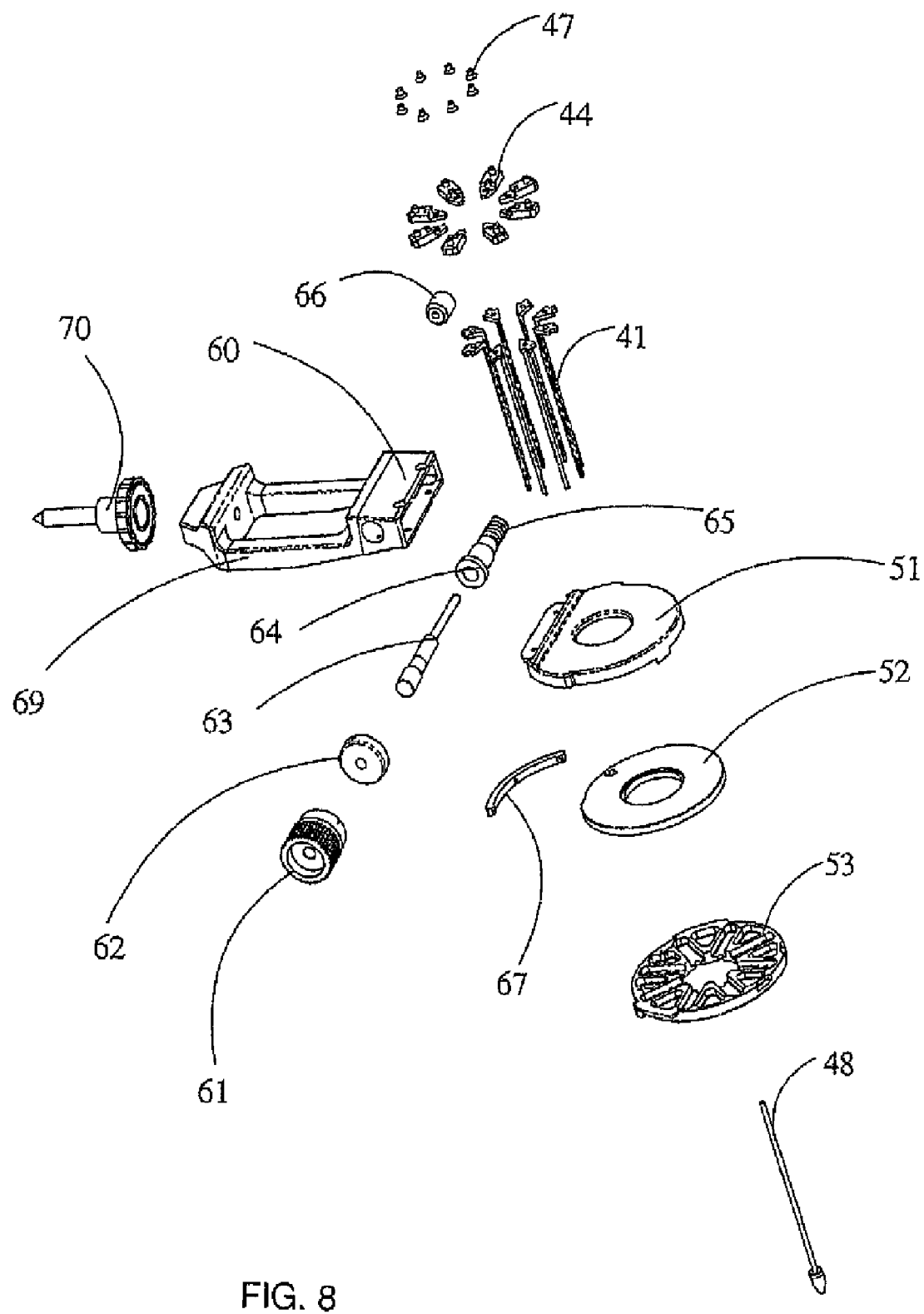
FIG. 8 is an exploded view of an improved radial expansible retractor according to the present invention.

FIG. 8 is an exploded view of a preferred embodiment of an improved radial expansible retractor 400 according to the present invention. The illustration shows the following parts of the improved radial expansible retractor 400:

The rib carrier bolt 47 designated to carry the rib carrier 44 to the rib 41, the cover disc 51 and the channeled disc 53, creating in unison a packaging which allows limited rotation movement of the grooved disc 52 and the tooth rail 67 designated to connect to the grooved disc, preferably to a depression in its circumference, while the tooth rail 67 has teeth facing outwards designated to gain motive force for rotational movement of the grooved disc 52, the central rod 48, the fixation bolt 70, and the adaptor 69, which is designated to adapt the packaging formed by the cover disc 51 and the channeled disc 53, and serves as a housing for some of the rotational movement transmission components and adjacent components also including the rotating wheel 61, which is the first component initiating the motion, by force of the operator's hand, the measure wheel 62, the shaft 63 which is connected to rotating wheel 61 and transmits the rotational movement to worm 65 which is connected to shaft 63 which has a spiral tooth in dimensions suitable to the dimension of the teeth of the tooth rail 67 such that the improved radial expansible retractor 400 has the spiral tooth of worm 65, combined with the teeth of the tooth rail 67, assembled to it, therefore the rotational movement initiated by rotating wheel 61 moves the grooved disc 52 rotationally around a rotational axis perpendicular to that of the rotating wheel 61. Shaft 63 rotates within front sleeve 64 and inner bearing 66.

The friction in the motive system is suitable for gentle transmission of motion and sufficient for the pressure on the ribs 41 created by the tissue does not close them undesirably.

Figure 9A:
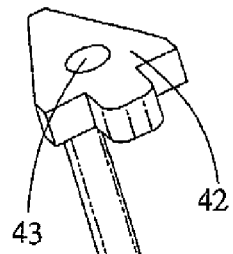
FIGS. 9a and 9b a are schematic perspective view illustrations of a rib and of a rib base, respectively, of an improved radial expansible retractor according to the present invention.

FIG. 9a, is a schematic perspective view illustration of a rib 41 of a preferred embodiment of an improved radial expansible retractor 400 according to the present invention. At one end of rib 41, the rib's base 42 is disposed, into which the rib base hole 43 is perforated, enabling connection by means of a bolt to the rib carrier 44. Rib 41 is formed as an elongated rod whose cross section can have many various geometrical shapes, also including the shape of a section of the wall of a cylinder, as in the present embodiment.

Figure 9B:
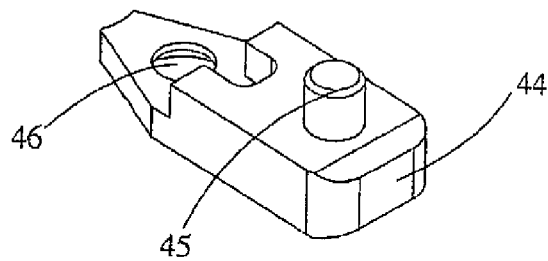
Figure 9C:
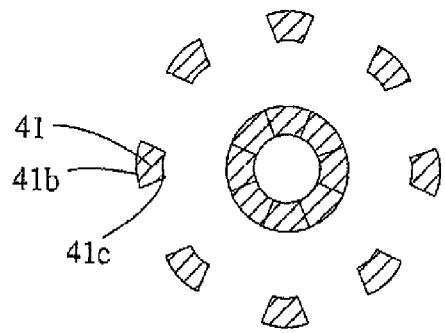
FIGS. 9c, 9d, and 9e are schematic cross sections of the ribs.

Rib 41 has a leading edge 41a and an external surface and an internal surface, such that as shown in FIG. 9c, on the external surface of rib 41, a pressure sensor 40 can be disposed, enabling real time measurement of the CPP.

FIG. 9b, is a schematic perspective view illustration of a rib base 42 of a preferred embodiment of an improved radial expansible retractor 400 according to the present invention. Its shape conforms for connection to the rib's base 42 and it includes rib carrier hole 46, and rib carrier pin 45.

This preferred embodiment enables exchanging rib 41 with another rib as necessary, for example a rib of a different length, cross section, etc.

According to another preferred embodiment, the rib and the rib base, including the pin, are made as a single part.

FIG. 9c is a schematic cross section of ribs 41 along the section line a-a as marked in FIG. 3c. The center of the illustration shows eight ribs 41 in closed mode, touching each other and forming a closed shape, in this case of a circular cylinder, namely each rib 41 has a cross section in the shape of a 45-degree segment of a circular cylinder wall. The perimeter of the illustration shows an opened mode of the ribs 41, after they have been distanced from each other, in this specific case at an identical distance of opening. Rib 41 has a rib internal surface 41c, and a rib external surface 41b.

Figure 9D:
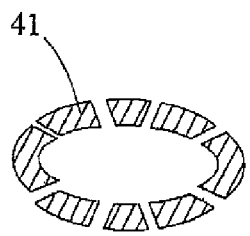

FIG. 9d is a schematic cross section of ribs 41 along the section line a-a as marked in FIG. 3c. The center of the illustration shows eight ribs 41 in nearly closed mode, almost touching each other, and forming a closed shape, in this case of an elliptical cylinder, namely each rib 41 has a cross section of a segment of an elliptical cylinder wall, in the specific case shown in the illustration different ribs of the eight differ from each other in cross section shapes.

Figure 9E:
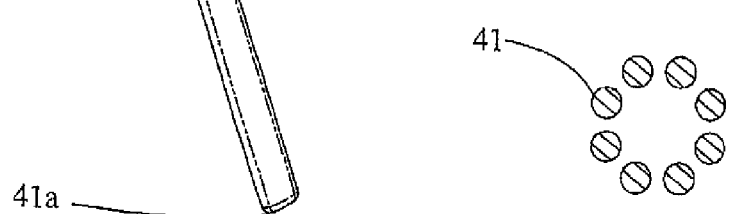

FIG. 9e is a schematic cross section of ribs 41 along the section line a-a as marked in FIG. 3c. The center of the illustration shows eight ribs 41 in nearly closed more, almost touching each other, while each of the ribs 41 has a circular cross section.

Figure 10A:
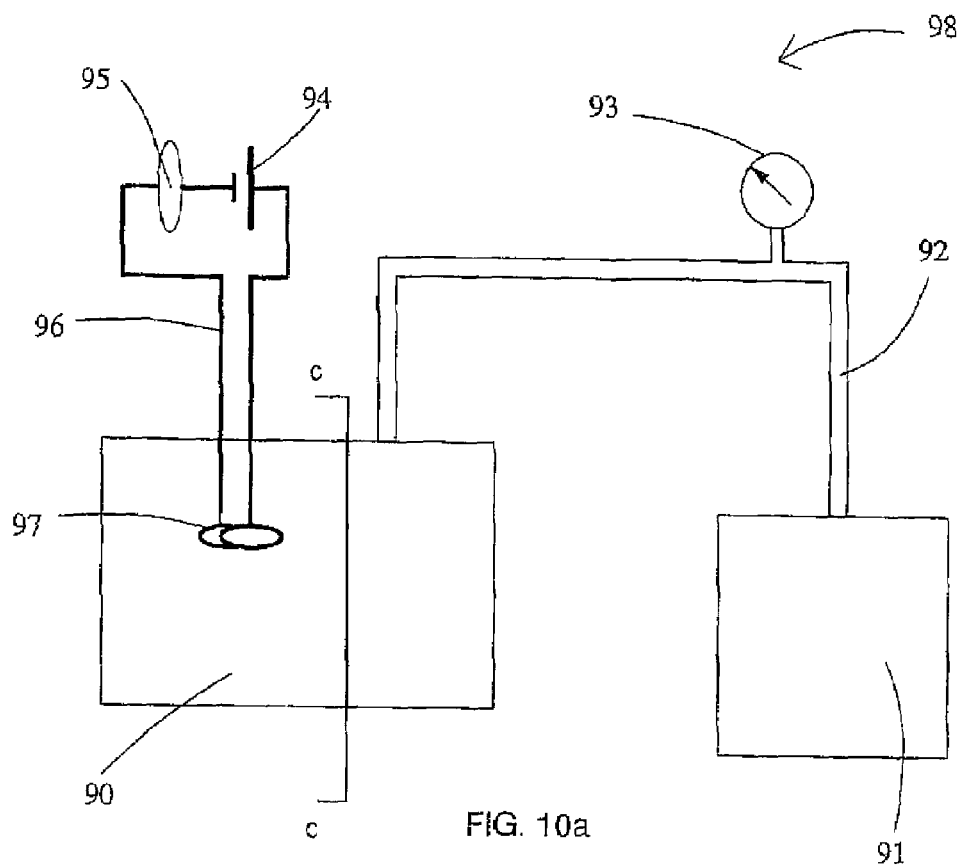
FIG. 10a is a schematic illustration of a subsystem for Brain Tissue Retraction Pressure (BTRP) measurement of the tissue which is in contact with the improved radial expansible retractor, according to the present invention.

FIG. 10a is a schematic illustration of a subsystem for BTRP measurement of the tissue 98 according to the present invention.

Knowing the level of pressures exerted by the retractor on the tissue it comes into contact with, when performing a medical procedure and especially when the ribs 41 are open, is extremely important. According to the present invention, folded bags 90 can be disposed in various places along the retractor inserted between tissues or into tissue. The location of a folded bag 90 monitor depression on the external surface of a rib 41 or between the ribs, namely between the tubule 49 and flexible sleeve 50, in which case the folded bag 90 is inserted into place only after insertion of the tubule 49 between the ribs 41.

The subsystem for measurement of the pressure on the tissue 98 includes one or more folded bags 90, which can be of polyethylene or any other suitable material. Pipeline 92 is connected to the folded bag 90 for the purpose of filling it with air, and pipeline 92 is also connected to air source, or any other suitable fluid, pressure source 91, which can be a compressed air container or a pump etc. In addition, there is a pressure gauge 93 connected to the pipeline.

Pressure measurement is started by increasing the pressure of the air in the folded bag 90 by means of the pressure source 91. As soon as the pressure in the bag 90 equals the pressure exerted on the folded bag 90 by the tissue with which it is in contact, the pressure gauge 93 gives a reading.

A miniature control light bulb 95, which indicates lack of pressure measurement, can optionally be added to the subsystem for measurement of the pressure on the tissue 98. The light is connected to electrical wire 96, and is supplied from an electrical power source 94. At each end of electrical wire 96, disposed within folded bag 90, there is an electrical contact element 97. When the elements 97 touch each other, the electrical circuit is closed and miniature control light bulb 95 goes on. This state occurs when there is no air pressure in folded bag 90, meaning that the pressure on the tissue 98 is not being measured at the moment.

Figure 10B:
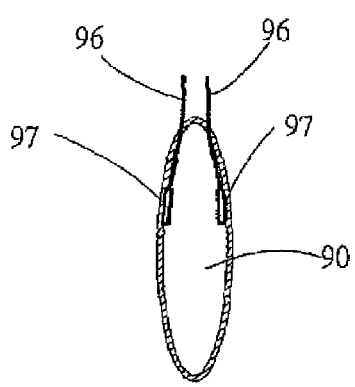
FIG. 10b is a schematic cross section of a component of the subsystem for BTRP measurement of the tissue according to the present invention.

FIG. 10b is a schematic cross section illustration of the folded bag 90 of FIG. 10a along line c-c. The illustration shows both electrical contact elements 97 attached to the insides of the folded bag 90, when they are separated from each other seeing as folded bag 90 has internal air pressure and is inflated. In this case miniature control light bulb 95 is off.

Figure 10C:
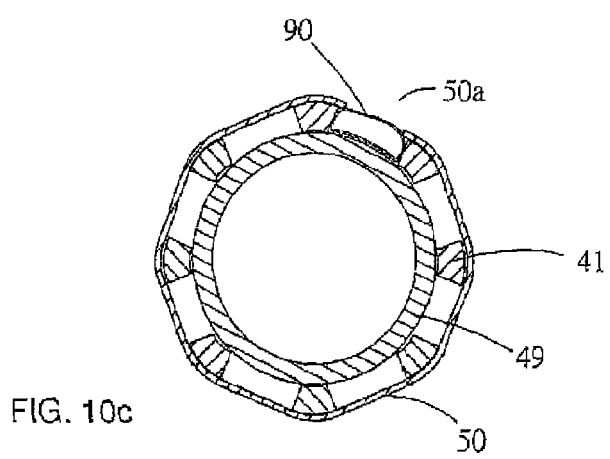
FIG. 10c is a schematic illustration of a component of the subsystem for BTRP measurement of the tissue disposed between the ribs of the retractor according to the present invention.

FIG. 10c is a schematic cross section along the section line a-a as marked in FIG. 3c through folded bag 90 which is disposed between the ribs 41 according to the present invention.

Folded bag 90 is disposed in the gap formed between two adjacent ribs 41 which are external to the tubule 49 facing a window of flexible sleeve 50a. The location facing the window of flexible sleeve 50a ensures that pressure exerted by the flexible sleeve 50 will not be mistakenly measured.

Additional folded bags 90 can be disposed between other ribs 41, as well as in other sections along the ribs 41, to enable collection of pressure data from numerous points.

Figure 11:
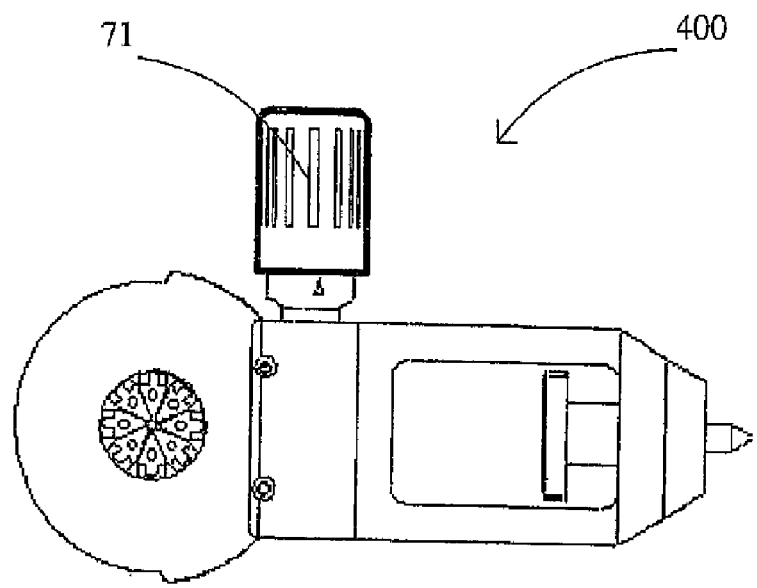
FIG. 11 is a schematic illustration of an improved radial expansible retractor, with an opening engine mechanism according to the present invention.

FIG. 11 is a schematic illustration of an improved radial expansible retractor 400, equipped with an opening engine 71 mechanism, according to another preferred embodiment of the present invention. Engine 71 provides the necessary rotational moment for operation of the improved radial expansible retractor 400, which can be controlled manually by the operator and can also be controlled automatically by a control system which also receives input of real time pressure data.

Figure 12:
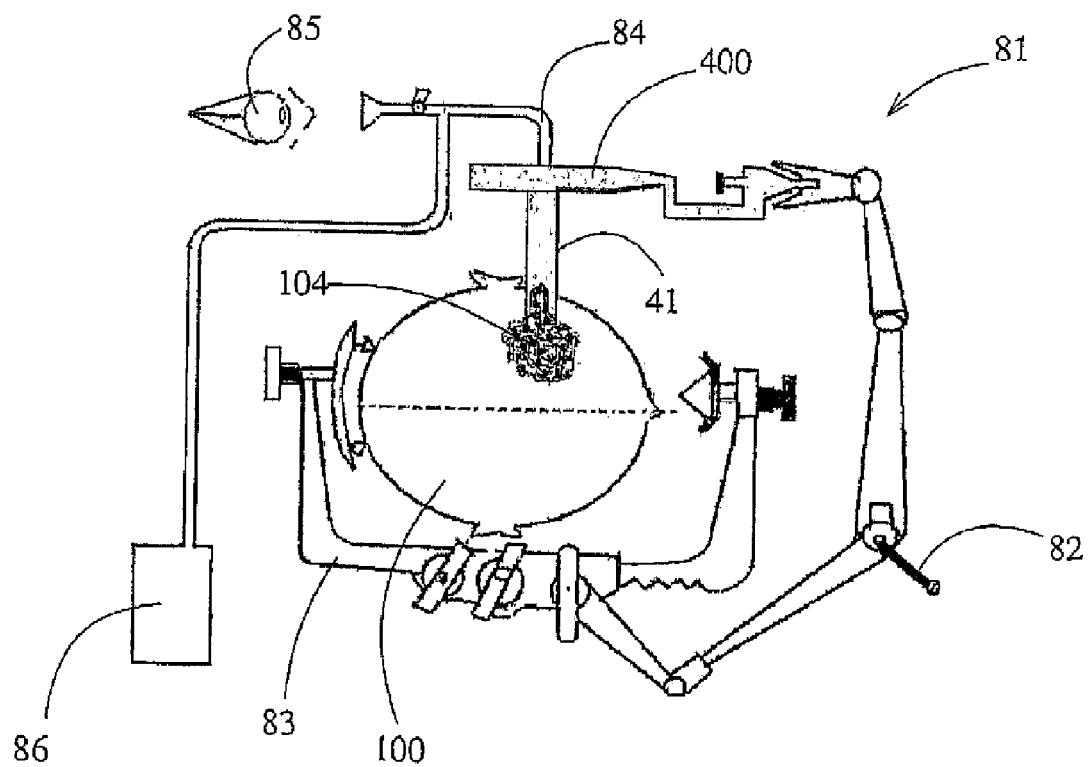
FIG. 12 is a schematic illustrations of an improved radial expansible retractor stationed during operation according to the present invention, in action.

FIG. 12 is a schematic illustration of a preferred embodiment of an improved radial expansible retractor 400 according to the present invention, in action.

The improved radial expansible retractor 400 is easily affixed to existing skull clamps and holder devices for use in neurosurgery.

The drawing illustrates the compatibility of the improved radial expansible retractor 400 with existing skull holding mechanisms. The improved radial expansible retractor 400 is securely held in place by a skull clamp joined to a holder device 81 locked by means of lock 82.

An endoscope 84, through which the doctor's eye 35 looks, is inserted into the canal together with a suction device 86 to access and remove, for example, an intracerebral hemorrhage (a) (ICH) 104.

As the improved radial expansible retractor 400 can come in many sizes, there is wide range of surgical specialties that can apply the device in their surgical procedures including general surgery, orthopedic surgery, ENT, vascular surgery, gynecology, urology, pediatric surgery, biopsy, and robotic technique. Cardiac surgery can make use of the device for insertions between the ribs and the insertion of an endoscope into the coronary artery to carry out bypass surgery without the need to cut and open the sternum. Multiple bone fractions can be reset using the device to realign bones and insert plates minimizing incision size and blood loss. The device allows for easy access for abdominal laparoscopic cholecystectomy. Chemotherapy can be applied directly to pathological cells with minimal damage to surrounding healthy cells.

Figure 13:
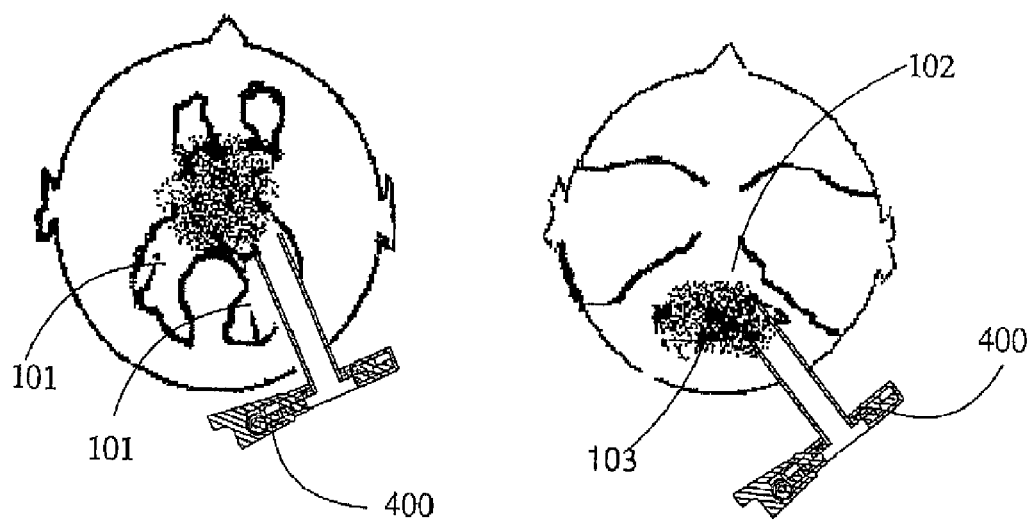
FIG. 13 is an illustration of a procedure to remove intra-ventricular hemorrhage from the lateral ventricle or to remove intra-ventricular hemorrhage from the fourth ventricle, using the improved radial expansible retractor, according to the present invention.

FIG. 13 is an illustration of the procedure to remove intraventricular hemorrhage from the lateral ventricle 101 or to remove intraventricular hemorrhage from the fourth ventricle 102, using the improved radial expansible retractor 400 to access the hemorrhage 103. The device allows access to areas of the brain previously almost impossible to access.

Figure 14:
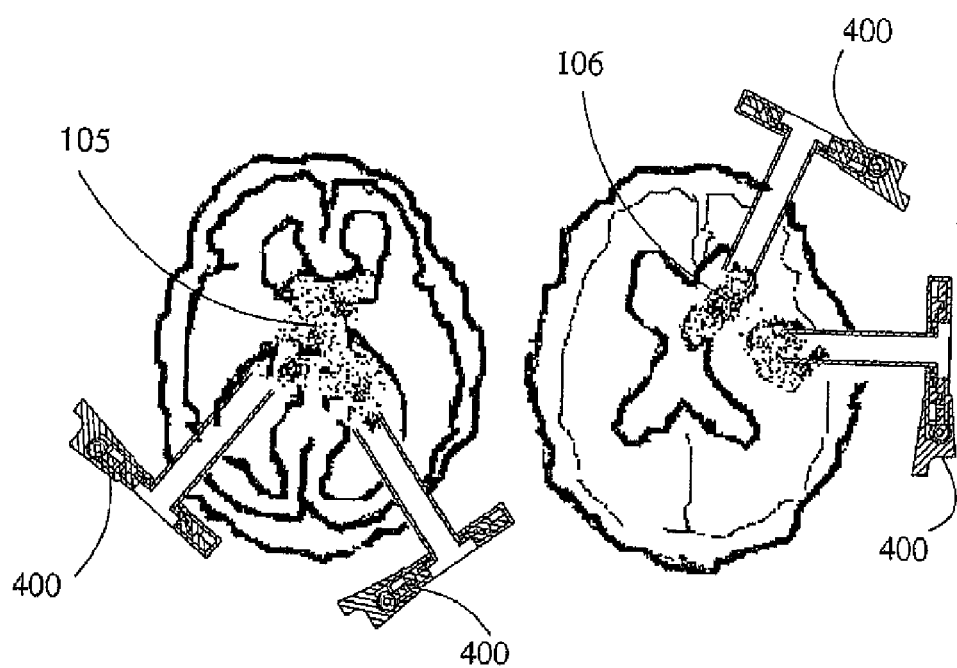
FIG. 14 shows a multi-portal approach to intra-ventricular hemorrhaging and intra-cerebral hemorrhaging with the improved radial expansible retractor being inserted from two separate sites easily accessing the hemorrhage and removing it by suction, according to the present invention.

FIG. 14 shows a multi-portal approach to intraventricular hemorrhaging 105 and intracerebral hemorrhaging (b) 106 with the improved radial expansible retractor 400 being inserted from two separate sites a and b to easily access the hemorrhage and suction it out.

Figure 15:
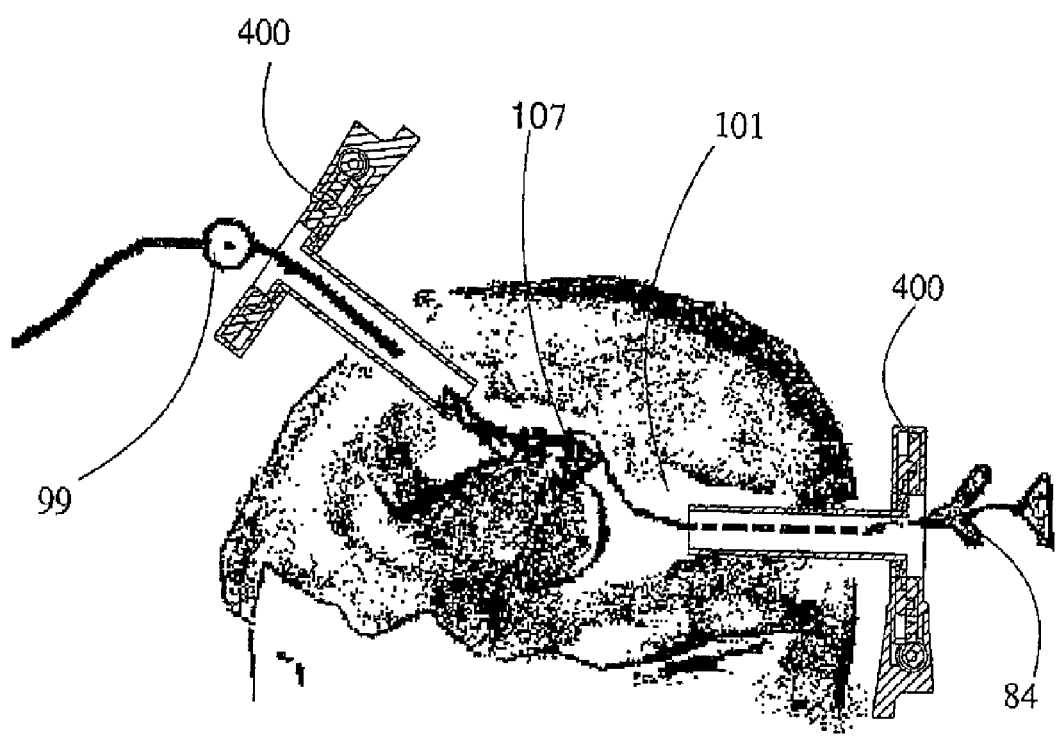
FIG. 15 shows a multi-portal removal of intra-ventricular lesions with an aspirator inserted into the expanded cannel from one side and an endoscope inserted via a second cannel, both through separated improved radial expansible retractor, according to the present invention.

FIG. 15 shows a multi-portal removal of intra-ventricular lesions 107 with an aspirator 99 inserted into the expanded canal from one side and an endoscope 94 inserted via a second canal, both through separated improved radial expansible retractor 400.

Some of the advantages of the improved radial expansible retractor according to the present invention follow:

It offers minimally invasive surgical solutions for many patients who at present face a bleak outlook.

There will be a drastic reduction in brain damage caused by lengthy and uncontrolled retraction of brain tissue.

It will shorten the time of operation. Operations that presently take 9-12 hours will take 1-2 hours.

Minimal openings in the skull will be no more than 10 to 20 mm.

Multiple tumors and metastases ran be removed in one surgical procedure, entering the brain at different points, with easier access and minimal damage to surrounding tissue.

Treatment of brain tumors with radiation applied via the retractor working channel directly to pathological cells will greatly reduce peripheral tissue damage and increase survival rates.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A radial expansible retractor for minimally invasive surgery for opening a channel in the brain and in any other soft tissue of a patient, by inserting part of the radial expansible retractor into the body of the patient, and by widening the channel at a continuous and gentle rate, the radial expansible retractor comprising:
   (a) a grooved disc having a central perforation, a cylindrical surface at the circumference of said grooved disc, and at least three grooves wherein said grooved disc defines an imaginary orthogonal coordinate system having X, Y, and Z axes, wherein said Z axis substantially passes through the center of said central perforation of said grooved disc, and wherein said grooved disc substantially lays on an imaginary plane, perpendicularly to said Z axis, wherein each of said grooves have an continuous curved shape on a plane perpendicular to said Z axis, wherein each of said grooves has three dimensional geometrical shape and size;
   (b) a channeled disc disposed at a position relative to said grooved disc, having at least three channels, wherein said channeled disc substantially lays on an imaginary plane, perpendicularly to said Z axis, and wherein said Z axis substantially passes through the center of said central perforation of said channeled disc, wherein each of said channels has three dimensional geometrical shape and size, wherein each of said channels extends radially in a direction on a plane perpendicular to said Z axis, wherein said radial extension starts at said Z axis, wherein said grooved disc can rotate at certain angle limits around said Z axis and thereby changing said position of said channeled disc relative to said grooved disc;
   (c) at least three ribs defining a channel having a cross sectional size, wherein each of said ribs has a base, a leading edge, and a cross section shape, wherein each of said ribs is laid substantially in parallel to said Z axis;
   (d) at least three carriers wherein each of said carriers is connected to said base of one of said ribs, so that each of said ribs is connected to one of said carriers, wherein each of said carriers has three dimensional geometrical shape and size, conforming to said geometrical shape and size of said channels, wherein each of said carriers includes:
      (i) a pin having three dimensional geometrical shape and size, conforming to said geometrical shape and size of said grooves, wherein each of said carriers is located inside one of said channels, and wherein each of said pins is located inside one of said grooves, so that a change of a relative position of said channeled disc relative to said grooved disc, which is expressed in a change of the angle between them on the plane perpendicular to said Z axis, causes a change of distance of each of said ribs from said Z axis, while said change of distance can be performed gently and continuously;
   (e) a cover disc having a central perforation and a cylindrical wall, and wherein said Z axis substantially passes through the center of said central perforation of said cover disc, wherein said channeled disc and said cover disc together form a package inside which a grooved disc is disposed;
   (f) at least three bolts, wherein said each of said rib bases and each of said rib carriers has a hole and wherein each one of said bolts connects one of said rib carriers to one of said rib bases, so that each one of said rib bases is connected to one of said rib carriers and each one of said rib carriers is connected to one of said rib bases;

(g) a tooth rail disposed on said cylindrical surface at the circumference of said grooved disc;

(h) a handle housing disposed on said cover disc and on said channeled disc;

(i) a worm, wherein said worm is positioned inside said handle housing, adjacent to said tooth rail such that when said worm performs rotational movement around an imaginary axis on a plane perpendicular to Z axis, it transmits mechanical movement to said tooth rail, thus granting rotational movement to said grooved disc around Z axis;

(j) a shaft disposed on said worm, inside said handle housing;

(k) a front sleeve disposed around said shaft, inside said handle housing;

(l) an inner bearing disposed around said shaft, inside said handle house;

(m) an adaptor disposed on said handle housing;

(n) a central rod having tail and head, wherein said head has a dome shape, wherein said central rod can be inserted between said ribs and pulled out from between them;

(o) a tubule, wherein said tubule can be inserted between said ribs and pulled out from between said ribs and pulled out from between them; and (p) a flexible sleeve, wherein said flexible sleeve can be pulled over said ribs; and pulled off of them.

2. The radial expansible retractor of claim 1, wherein said tubule is composed of a translucent material and has at least one perforation, and wherein said flexible sleeve is composed of a translucent material.

3. A radial expansible retractor for minimally invasive surgery for opening a channel in the brain and in any other soft tissue of a patient, by inserting part of the radial expansible retractor into the body of the patient, and by widening the channel at a continuous and gentle rate, the radial expansible retractor comprising:

(a) a grooved disc having a central perforation, a cylindrical surface at the circumference of said grooved disc, and at least three grooves wherein said grooved disc defines an imaginary orthogonal coordinate system having X, Y, and Z axes, wherein said Z axis substantially passes through the center of said central perforation of said grooved disc, and wherein said grooved disc substantially lays on an imaginary plane, perpendicularly to said Z axis, wherein each of said grooves have an continuous curved shape on a plane perpendicular to said Z axis, wherein each of said grooves has three dimensional geometrical shape and size;

(b) a channeled disc disposed at a position relative to said grooved disc, having at least three channels, wherein said channeled disc substantially lays on an imaginary plane, perpendicularly to said Z axis, and wherein said Z axis substantially passes through the center of said central perforation of said channeled disc, wherein each of said channels has three dimensional geometrical shape and size, wherein each of said channels extends radially in a direction on a plane perpendicular to said Z axis, wherein said radial extension starts at said Z axis, wherein said grooved disc can rotate at certain angle limits around said Z axis and thereby changing said position of said channeled disc relative to said grooved disc;

(c) at least three ribs defining a channel having a cross sectional size, wherein each of said ribs has a base, a leading edge, and a cross section shape, wherein each of said ribs is laid substantially in parallel to said Z axis;

(d) at least three carriers wherein each of said carriers is connected to said base of one of said ribs, so that each of said ribs is connected to one of said carriers, wherein each of said carriers has three dimensional geometrical shape and size, conforming to said geometrical shape and size of said channels, wherein each of said carriers includes:

(i) a pin having three dimensional geometrical shape and size, conforming to said geometrical shape and size of said grooves, wherein each of said carriers is located inside one of said channels, and wherein each of said pins is located inside one of said grooves, so that a change of a relative position of said channeled disc relative to said grooved disc, which is expressed in a change of the angle between them on the plane perpendicular to said Z axis, causes a change of distance of each of said ribs from said Z axis, while said change of distance can be performed gently and continuously;

(e) a cover disc having a central perforation and a cylindrical wall, and wherein said Z axis substantially passes through the center of said central perforation of said cover disc, wherein said channeled disc and said cover disc together form a package inside which a grooved disc is disposed;

(f) at least three bolts, wherein said each of said rib bases and each of said rib carriers has a hole and wherein each one of said bolts connects one of said rib carriers to one of said rib bases, so that each one of said rib bases is connected to one of said rib carriers and each one of said rib carriers is connected to one of said rib bases;

(g) a tooth rail disposed on said cylindrical surface at the circumference of said grooved disc;

(h) a handle housing disposed on said cover disc and on said channeled disc;

(i) a worm, wherein said worm is positioned inside said handle housing, adjacent to said tooth rail such that when said worm performs rotational movement around an imaginary axis on a plane perpendicular to Z axis, it transmits mechanical movement to said tooth rail, thus granting rotational movement to said grooved disc around Z axis;

(j) a shaft disposed on said worm, inside said handle housing;

(k) a front sleeve disposed around said shaft, inside said handle housing;

(l) an inner bearing disposed around said shaft, inside said handle house;

(m) a rotating wheel disposed on said shaft, wherein said radial expansible retractor has at least eight ribs, wherein said grooved disc has at least eight grooves, and wherein said channeled disc has at least eight channels, wherein at least one of said grooves' continuous curves has a shape differing from that of at least one of the other grooves continuous curves.

4. A radial expansible retractor for minimally invasive surgery for opening a channel in the brain and in any other soft tissue of a patient, by inserting part of the radial expansible retractor into the body of the patient, and by widening the channel at a continuous and gentle rate, the radial expansible retractor comprising:

(a) a grooved disc having a central perforation, a cylindrical surface at the circumference of said grooved disc, and at least three grooves wherein said grooved disc defines an imaginary orthogonal coordinate system having X, Y, and Z axes, wherein said Z axis substantially passes the center of said central perforation of said grooved disc, and wherein said grooved disc substantially lays on an imaginary plane, perpendicularly to said Z axis, wherein each of said grooves have an continuous curved shape on a plane perpendicular to said Z axis, wherein each of said grooves has three dimensional geometrical shape and size;

(b) a channeled disc disposed at a position relative to said grooved disc, having at least three channels, wherein said channeled disc substantially lays on an imaginary plane, perpendicularly to said Z axis, and wherein said Z axis substantially passes through the center of said central perforation of said channeled disc, wherein each of said channels has three dimensional geometrical shape and size, wherein each of said channels extends radially in a direction on a plane perpendicular to said Z axis, wherein said radial extension starts at said Z axis, wherein said grooved disc can rotate at certain angle limits around said Z axis and thereby changing said position of said channeled disc relative to said grooved disc;

(c) at least three ribs defining a channel having a cross sectional size, wherein each of said ribs has a base, a leading edge, and a cross section shape, wherein each of said ribs is laid substantially in parallel to said Z axis;

(d) at least three carriers wherein each of said carriers is connected to said base of one of said ribs, so that each of said ribs is connected to one of said carriers, wherein each of said carriers has three dimensional geometrical shape and size, conforming to said geometrical shape and size of said channels, wherein each of said carriers includes:

(i) a pin having three dimensional geometrical shape and size, conforming to said geometrical shape and size of said grooves, wherein each of said carriers is located inside one of said channels, and wherein each of said pins is located inside one of said grooves, so that a change of a relative position of said channeled disc relative to said grooved disc, which is expressed in a change of the angle between them on the plane perpendicular to said Z axis, causes a change of distance of each of said ribs from said Z axis, while said change of distance can be performed gently and continuously;

(e) a cover disc having a central perforation and a cylindrical wall, and wherein said Z axis substantially passes through the center of said central perforation of said cover disc, wherein said channeled disc and said cover disc together form a package inside which a grooved disc is disposed;

(f) at least three bolts, wherein said each of said rib bases and each of said rib carriers has a hole and wherein each one of said bolts connect one of said rib carriers to one of said rib bases, so that each one of said rib bases is connected to one of said rib carriers and each one of said rib carriers is connected to one of said rib bases;

(g) a tooth rail disposed on said cylindrical surface at the circumference of said grooved disc;

(h) a handle housing disposed on said cover disc and on said channeled disc;

(i) a worm, wherein said worm is positioned inside said handle housing, adjacent to said tooth rail such that when said worm performs rotational movement around an imaginary axis on a plane perpendicular to Z axis, it transmits mechanical movement to said tooth rail, thus granting rotational movement to said grooved disc around Z axis;

(j) a shaft disposed on said worm, inside said handle housing;

(k) a front sleeve disposed around said shaft, inside said handle housing;

(l) an inner bearing disposed around said shaft, inside said handle house;

(m) a rotating wheel disposed on said shaft, wherein said radial expansible retractor having at least eight ribs, wherein said grooved disc has at least eight grooves, and wherein said channeled disc has at least eight channels, wherein each of said grooves' continuous curves shape has the same curved shape, wherein each of said grooves' continuous curves has a first end and a second end, wherein said groove's continuous curve has a first angle measured between said continuous curve's direction at said first end and the direction of a radius starting at Z axis passing through said first end, wherein said groove's continuous curve has a second angle measured between said continuous curve's direction at said second end and die direction of a radius starting at Z axis passing through said second end, and wherein said second angle is at least three degrees larger, and at most eight degrees larger, than said first angle.

5. A radial expansible retractor for minimally invasive surgery for opening a channel in the brain and in any other soft tissue of a patient, by inserting part of the radial expansible retractor into the body of the patient, and by widening the channel at a continuous and gentle rate, the radial expansible retractor comprising:

(a) a grooved disc having a central perforation, a cylindrical surface at the circumference of said grooved disc, and at least three grooves wherein said grooved disc defines an imaginary orthogonal coordinate system having X, Y, and Z axes, wherein said Z axis substantially passes through the center of said central perforation of said grooved disc, and wherein said grooved disc substantially lays on an imaginary plane, perpendicularly to said Z axis, wherein each of said grooves has a continuous curved shape on a plane perpendicular to said Z axis, wherein each of said grooves has three dimensional geometrical shape and size;

(b) a channeled disc disposed at a position relative to said grooved disc, having at least three channels, wherein said channeled disc substantially lays on an imaginary plane, perpendicularly to said Z axis, and wherein said Z axis substantially passes through the center of said central perforation of said channeled disc, wherein each of said channels has three dimensional geometrical shape and size, wherein each of said channels extends radially in a direction on a plane perpendicular to said Z axis, wherein said radial extension starts at said Z axis, wherein said grooved disc can rotate at certain angle limits around said Z axis and thereby changing said position of said channeled disc relative to said grooved disc;

(c) at least three ribs defining a channel having a cross sectional size, wherein each of said ribs has a base, a leading edge, and a cross section shape, wherein each of said ribs is laid substantially in parallel to said Z axis;

(d) at least three carriers wherein each of said carriers is connected to said base of one of said ribs, so that each of said ribs is connected to one of said carriers, wherein each of said carriers has three dimensional geometrical shape and size, conforming to said geometrical shape and size of said channels, wherein each of said carriers includes:
  (i) a pin having three dimensional geometrical shape and size, conforming to said geometrical shape and size of said grooves, wherein each of said carriers is located inside one of said channels, and wherein each of said pins is located inside one of said grooves, so that a change of a relative position of said channeled disc relative to said grooved disc, which is expressed in a change of the angle between them on the plane perpendicular to said Z axis, causes a change of distance of each of said ribs from said Z axis, while said change of distance can be performed gently and continuously
  (e) a cover disc having a central perforation and a cylindrical wall, and wherein said Z axis substantially passes through the center of said central perforation of said cover disc, wherein said channeled disc and said cover disc together form a package inside which a grooved disc is disposed;
(f) at least three bolts, wherein said each of said rib bases and each of said rib carriers has a hole and wherein each one of said bolts connect one of said rib carriers to one of said rib bases, so that each one of said rib bases is connected to one of said rib carriers and each one of said rib carriers is connected to one of said rib bases;
(g) a tooth rail disposed on said cylindrical surface at the circumference of said grooved disc;
(h) a handle housing disposed on said cover disc and on said channeled disc;
(i) a worm, wherein said worm is positioned inside said handle housing, adjacent to said tooth rail such that when said worm performs rotational movement around an imaginary axis on a plane perpendicular to Z axis, it transmits mechanical movement to said tooth rail, thus granting rotational movement to said grooved disc around Z axis;
(j) a shaft disposed on said worm, inside said handle housing;
(k) a front sleeve disposed around said shaft, inside said handle housing;
(l) an inner bearing disposed around said shaft, inside said handle house, wherein each of said ribs cross section shape is of a segment of a cylindrical wall, while the combination of all of said cross section shapes can form a cross section shape of a cylindrical wall, and wherein each of said ribs has an internal surface, and an external surface;
(m) a flexible sleeve, wherein said flexible sleeve can be pulled over said ribs and pulled off of them; and
(n) at least one subsystem for real time measurement and monitoring of the Brain Retraction Pressure (BRP), said subsystem for measurement of the pressure on tissue including:
  (i) a folded bag disposed in a gap formed between two adjacent said ribs;
  (ii) an air pipeline connected to said folded bag;
  (iii) an air pressure source connected to said pipeline; and
  (iv) an air pressure gauge connected to said pipeline, wherein said flexible sleeve has a window and wherein said folded bag is disposed facing said flexible sleeve window.

6. The radial expansible retractor of claim 5 wherein the subsystem for measurement of the pressure on tissue, further including:
  (v) an electrical power source;
  (vi) electrical wires connected to said power source;
  (vii) a miniature control light bulb connected to said electrical wires; and
  (viii) two electrical contact elements connected to said electrical wires and attached to the insides of said folded bag such that when said folded bag is not inflated both of said contact elements touch each other and said miniature control light bulb is switched on, and when said folded bag is inflated both of said contact elements are separated from each other and said miniature control light bulb is switched off.

7. The radial expansible retractor of claim 6, wherein said electrical power source of said subsystem for measurement of the pressure on tissue is a battery.

8. The radial expansible retractor of claim 5, wherein said folded bag is a folded polyethylene bag.

9. A method of minimally invasive surgery, comprising the steps of:
(a) providing a radial expansible retractor for minimally invasive surgery for opening a channel in the brain of a patient, by inserting the radial expansible retractor into the brain of the patient, and by widening the channel at a continuously and gentle rate, said radial expansible retractor including:
  (i) a grooved disc having a central perforation, a cylindrical surface at the circumference of said grooved disc; and at least three grooves wherein said grooved disc defines an imaginary orthogonal coordinate system having X, Y, and Z axes, wherein said Z axis substantially passes through the center of said central perforation of said grooved disc, and wherein said grooved disc substantially lies on an imaginary plane, perpendicularly to said Z axis, wherein each of said grooves has an continuous curved shape on a plane perpendicular to said Z axis, wherein each of said grooves has three dimensional geometrical shape and size;
  (ii) a channeled disc disposed at a position relative to said grooved disc, having at least three channels wherein said channeled disc substantially lies on an imaginary plane, perpendicularly to said Z axis, and wherein said Z axis substantially passes through the center of said central perforation of said channeled disc, wherein each of said channels has three dimensional geometrical shape and size, wherein each of said channels extends radially in a direction on a plane perpendicular to said Z axis, wherein said radial extension starts at said Z axis, wherein said grooved disc can be rotated at certain angle limits around said Z axis and thereby changing said position of said channeled disc relative to said grooved disc;
  (iii) at least three ribs defining a channel having a cross sectional size, wherein each of said ribs has a base, a leading edge, and a cross section shape, wherein each of said ribs is laid in parallel to said Z axis; and
  (iv) at least three carriers wherein each of said carriers is connected to said base of one of said ribs, so that each of said ribs is connected to one of said carrier, wherein each of said carriers has three dimensional geometrical shape and size, conforming to said geometrical shape and size of said channels, wherein each of said carriers includes:
    (A) a pin having three dimensional geometrical shape and size, conforming to said geometrical shape and size of said grooves, wherein each of said carriers is located inside one of said channels, and wherein each of said pins is located inside one of said grooves, so that a change of a relative position of said channeled disc relative to said grooved disc, which is expressed in a change of the angle between them on the plane perpendicular to said Z axis, causes a change of distance of each of said ribs from said Z axis, while said change of distance can be performed gently and continuously; and (v) a cover disc having a central perforation and a cylindrical wall, and wherein said Z axis substantially passes through the center of said central perforation of said cover disc, wherein said channeled disc and said cover disc together form a package inside which a grooved disc is disposed;

(b) forming an opening in the exterior of a body portion located in proximity to a tissue portion in which hemorrhaging has occurred;

(c) inserting an radial expansible retractor ribs through said opening, through body tissue so as to reach said hemorrhage to be suctioned out;

(d) expanding said radial expansible ribs by distancing them from one another with radially linear movement from a joint center to cause a lateral multi-axial displacement of adjacent tissue so as to expose the hemorrhage;

(e) removing said hemorrhage by a suction;

(f) providing another radial expansible retractor for minimally invasive surgery for opening a channel in the brain of a patient;

(g) forming another opening in an exterior of a body portion located in proximity to a tissue portion where hemorrhaging has occurred;

(h) inserting another radial expansible retractor ribs though said another opening, through body tissue so as to reach said hemorrhage to be suctioned out;

(i) expanding said other radial expansible retractor ribs by distancing them from one another in radially linear movement from a joint center to cause a lateral multi-axial displacement of adjacent tissue so as to expose a hemorrhage; and (j) removing said hemorrhage.

* * * * *